US010925956B2

(12) United States Patent
Callendret et al.

(10) Patent No.: US 10,925,956 B2
(45) Date of Patent: Feb. 23, 2021

(54) METHODS AND COMPOSITIONS FOR INDUCING PROTECTIVE IMMUNITY AGAINST A MARBURG VIRUS INFECTION

(71) Applicants: Janssen Vaccines & Prevention B.V., Leiden (NL); Bavarian Nordic A/S, Kvistgaard (DK)

(72) Inventors: Benoit Christophe Stephan Callendret, The Hague (NL); Ramon Roozendaal, Utrecht (NL); Jutta Sytske Hartkoorn-Pasma, Leiden (NL); Ariane Volkmann, Andechs (DE); Robin Steigerwald, Munich (DE); Ulrike Dirmeier, Starnberg (DE)

(73) Assignees: Janssen Vaccines & Prevention B.V., Leiden (NL); Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 16/317,111

(22) PCT Filed: Jul. 14, 2017

(86) PCT No.: PCT/IB2017/054286

§ 371 (c)(1),
(2) Date: Jan. 11, 2019

(87) PCT Pub. No.: WO2018/011768

PCT Pub. Date: Jan. 18, 2018

(65) Prior Publication Data

US 2019/0224301 A1 Jul. 25, 2019

Related U.S. Application Data

(60) Provisional application No. 62/362,831, filed on Jul. 15, 2016.

(51) Int. Cl.
*A61K 39/12* (2006.01)
*A61K 39/00* (2006.01)

(52) U.S. Cl.
CPC ...... *A61K 39/12* (2013.01); *A61K 2039/5256* (2013.01); *A61K 2039/545* (2013.01); *C12N 2710/10343* (2013.01); *C12N 2710/24043* (2013.01); *C12N 2760/14134* (2013.01); *C12N 2760/14171* (2013.01); *C12N 2760/14234* (2013.01); *C12N 2760/14271* (2013.01)

(58) Field of Classification Search
CPC .............. A61K 2039/545; A61K 39/12; A61K 2039/5256; A61K 2039/5254; A61K 2039/572; A61K 2039/575; C12N 15/861; C12N 15/863; C07K 14/08; A61P 31/14; A01N 59/02; Y10S 530/826; G01N 33/56983

See application file for complete search history.

(56) References Cited

U.S. PATENT DOCUMENTS

| | | | |
|---|---|---|---|
| 5,185,146 | A | 2/1993 | Altenburger |
| 6,083,716 | A | 7/2000 | Wilson et al. |
| 6,761,893 | B2 | 7/2004 | Chaplin et al. |
| 7,270,811 | B2 | 9/2007 | Bout et al. |
| 9,526,777 | B2 | 12/2016 | Sullivan |
| 2003/0206926 | A1 | 11/2003 | Chaplin et al. |
| 2006/0159699 | A1 | 7/2006 | Howley et al. |
| 2010/0247522 | A1 | 9/2010 | Zhang |
| 2013/0101618 | A1 | 4/2013 | Sullivan |
| 2014/0017278 | A1 | 1/2014 | Sullivan |
| 2015/0361141 | A1 | 12/2015 | Buttigieg |

FOREIGN PATENT DOCUMENTS

| | | | |
|---|---|---|---|
| JP | 2005517639 | | 6/2005 |
| JP | 2014503206 | | 2/2014 |
| WO | 0000616 | | 1/2000 |
| WO | 0008131 | | 2/2000 |
| WO | 200070071 | A1 | 11/2000 |
| WO | 02/24224 | A2 | 3/2002 |
| WO | 02/42480 | A2 | 5/2002 |
| WO | 03/048184 | A2 | 6/2003 |
| WO | 03047617 | | 6/2003 |
| WO | 03048184 | | 6/2003 |
| WO | 2003104467 | A1 | 12/2003 |
| WO | 2004001032 | A2 | 12/2003 |
| WO | 2005071093 | A2 | 8/2005 |
| WO | 2006/037038 | A1 | 4/2006 |
| WO | 2007104792 | A2 | 9/2007 |
| WO | 2010057650 | A1 | 5/2010 |
| WO | 2010085984 | A1 | 8/2010 |
| WO | 2010086189 | A2 | 8/2010 |
| WO | 2011/092029 | A1 | 8/2011 |
| WO | 2012082918 | A1 | 6/2012 |
| WO | 2012106490 | A1 | 8/2012 |
| WO | 2013155441 | A1 | 10/2013 |
| WO | 2014006191 | A1 | 1/2014 |

(Continued)

OTHER PUBLICATIONS

Sullivan et al, "Immune Protection of Nonhuman Primates against Ebola Virus with Single Low-Dose Adenovirus Vectors Encoding Modified GPs," PLOS Medicine, vol. 3, No. 6, pp. 865-873 (Jun. 2006).
Tatsis et al, "A CD46-binding Chimpanzee Adenovirus Vector as a Vaccine Carrier," Molecular Therapy, vol. 15, No. 3, pp. 608-617 (Mar. 2007).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).
Peters et al, "Filoviridae: Marburg and Ebola Virues," Fields Virology, Ed. 3, pp. 1161-1167 (1996).
Sambrook et al, "Molecular Cloning—A Laboratory Manual," Ed. 2 (1989).

(Continued)

*Primary Examiner* — Bao Q Li
(74) *Attorney, Agent, or Firm* — Ice Miller LLP

(57) ABSTRACT

Compositions, vaccines and methods using a combination of adenovirus vectors and MVA vectors for inducing protective immunity against a Marburg virus infection are described.

18 Claims, 3 Drawing Sheets

Specification includes a Sequence Listing.

(56) References Cited

FOREIGN PATENT DOCUMENTS

| | | |
|---|---|---|
| WO | 2014037124 | 3/2014 |
| WO | 2016034678 A2 | 3/2016 |
| WO | 2016036955 A1 | 3/2016 |
| WO | 2016036971 A1 | 3/2016 |

OTHER PUBLICATIONS

Int'l Search Report dated Jan. 18, 2019 in Int'l Application No. PCT/IB2017/054286.

Abbink et al, "Comparative seroprevalence and immunogenicity of six rare serotype recombinant adenovirus vaccine vectors from subgroups B and D," Journal of Virology, vol. 81, No. 9, pp. 4654-4663 (2007).

Altschul et al, "Basic Local Alignment Search Tool," Journal of Molecular Biology, vol. 215, pp. 403-410 (1990).

Altschul et al, "Gapped BLASTand PSI-BLAST: a new generation of protein database search programs," Nucleic Acids Research, vol. 25, No. 17, pp. 3389-3402 (1997).

Ambrosini et al, "Gene transfer in astrocytes: Comparison between different delivering methods and expression of the HIV-1 protein Nef," Journal of Neuroscience Research, vol. 55, pp. 569-577 (1999).

Asmuth et al, "Comparative Cell-Mediated Immunogenicity of DNA/DNA, DNA/Adenovirus Type 5 (Ad5), or Ad5/Ad5 HIV-1 Clade B gag Vaccine Prime-Boost Regimens", The Journal of Infectious Diseases, vol. 201, pp. 132-141 (2010).

Bangari et al, "Development of nonhuman adenoviruses as vaccine vectors," Vaccine, vol. 24, No. 7, pp. 849-862 (2006).

Blanchard et al, " Modified vaccinia virus Ankara undergoes limited replication in human cells and lacks several immunomodulatory proteins: implications for use as a human vaccine," Journal of General Virology, vol. 79, pp. 1159-1167 (1998).

Boukamp et al, "Normal Keratinization in a Spontaneously Immortalized Aneuploid Human Keratinocyte Cell Line," Journal of Cell Biology, vol. 106, No. 3, pp. 761-771 (1988).

Buchbinder et al, "Efficacy assessment of a cell-mediated immunity HIV-1 vaccine (the Step Study): a double-blind, randomised, placebo-controlled, test-of-concept trial," The Lancet, vol. 372, No. 9653, pp. 1881-1893 (2008).

Carroll et al, "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).

Catanzaro et al, "Phase 1 Safety and Immunogenicity Evaluation of a Multiclade HIV-1 Candidate Vaccine Delivered by a Replication-Defective Recombinant Adenovirus Vector," Journal of Infectious Diseases, vol. 194, No. 12, pp. 1638-1649 (2006).

Cheng et al, "Mechanism of Ad5 Vaccine Immunity and Toxicity: Fiber Shaft Targeting of Dendritic Cells," PLOS, vol. 3, Issue 2, pp. 239-245 (e25) (2007).

Cohen et al, "Chimpanzee adenovirus CV-68 adapted as a gene delivery vector interacts with the coxsackievirus and adenovirus receptor," Journal of General Virology, vol. 83, Pt. 1, pp. 151-155 (2002).

Cosma et al, "Therapeutic vaccination with MVA-HIV-1 nef elicits Nef-specific T-helper cell responses in chronically HIV-1 infected individuals," Vaccine, vol. 22, No. 1, pp. 21-29 (2003).

Daddario-Dicaprio et al, "Cross-Protection against Marburg Virus Strains by Using a Live, Attenuated Recombinant Vaccine," Journal of Virology, vol. 80, No. 19, pp. 9659-9666 (2006).

De Gruijl et al, "Intradermal Delivery of Adenoviral Type-35 Vectors Leads to High Efficiency Transduction of Mature, CD8+ T Cell-Stimulating Skin-Emigrated Dendritic Cells," The Journal of Immunology, vol. 177, No. 4, pp. 2208-2215 (2006).

Di Nicola et al, "Immunization of Patients with Malignant Melanoma with Autologous CD34+ Cell-Derived Dendritic Cells Transduced Ex Vivo with a Recombinant Replication-Deficient Vaccinia Vector Encoding the Human Tyrosinase Gene: A Phase I Trial," Human Gene Therapy, vol. 14, pp. 1347-1360 (2003).

Di Nicola et al, "Boosting T Cell-Mediated Immunity to Tyrosinase by Vaccinia Virus-Transduced, CD34+-Derived Dendritic Cell Vaccination: A Phase I Trial in Metastatic Melanoma," Clinical Cancer Research, vol. 10, No. 16, pp. 5381-5390 (2004).

Farina et al, "Replication-Defective Vector Based on a Chimpanzee Adenovirus," Journal of Virology, vol. 75, No. 23, pp. 11603-11613 (2001).

Friedrich et al, "Potential Vaccines and Post-Exposure Treatments for Filovirus Infections," Viruses, vol. 4, pp. 1619-1650 (2012).

Harro et al, "Safety and Immunogenicity of the Merck Adenovirus Serotype 5 (MRKAd5) and MRKAd6 Human Immunodeficiency Virus Type 1 Trigene Vaccines Alone and in Combination in Healthy Adults," Clinical and Vaccine Immunology, vol. 16, No. 9, pp. 1285-1292 (2009).

Havenga et al, "Novel replication-incompetent adenoviral B-group vectors: high vector stability and yield in PER.C6 cells," Journal of General Virology, vol. 87, pp. 2135-2143 (2006).

Harrer et al, "Therapeutic vaccination of HIV-1-infected patients on HAART with a recombinant HIV-1 nef-expressing MVA: safety, immunogenicity and influence on viral load during treatment interruption," Antiviral Therapy, vol. 10, No. 2, pp. 285-300, (2003).

Haslett et al, "Strong Human Immunodeficiency Virus (HIV)-Specific CD4+ T Cell Responses in a Cohort of Chronically Infected Patients Are Associated with Interruptions in Anti-HIV Chemotherapy," Journal of Infectious Diseases, vol. 181, pp. 1264-1272 (2000).

Henikoff et al, "Amino acid substitution matrices from protein blocks," Proceedings of the National Academy of Sciences of the United States of America, vol. 89, No. 22, pp. 10915-10919 (Nov. 1992).

Hill et al, "Human Vaccines, Prime-boost vectored malaria vaccines: Progress and prospects," vol. 6, No. 1, pp. 78-83 (Jan. 2010).

Jin et al, "Stabilizing formulations for inhalable powders of an adenovirus 35-vectored tuberculosis (TB) vaccine (AERAS-402)," Vaccine, vol. 28, No. 27, pp. 4369-4375 (2010).

Karlin et al, "Applications and statistics for multiple high-scoring segments in molecular sequences," Proceedings of the National Academy of Sciences of the United States of America, vol. 90, pp. 5873-5877 (Jun. 1993).

Kibuuka et al, "A Phase I/II Study of a Multiclade HIV-1 DNA Plasmid Prime and Recombinant Adenovirus-type 5 Boost Vaccine in HIV Uninfected East Africans (RV 172)," The Journal of Infectious Diseases, vol. 201, No. 4, pp. 600-607 (Feb. 2010).

Kobinger et al, "Chimpanzee adenovirus vaccine protects against Zaire Ebola virus," Virology, vol. 346, pp. 394-401 (2006).

Koup et al, "Priming Immunization with DNA Augments Immunogenicity of Recombinant Adenoviral Vectors for Both HIV-1 Specific Antibody and T-Cell Responses," PLOS One, vol. 5, No. 2, p. e9015 (Feb. 2010).

Lasaro et al., "New insights on adenovirus as vaccine vectors.," Molecular Therapy, vol. 17, No. 8, pp. 1333-1339 (Aug. 2009).

Liu et al, "Immune control of an SIV challenge by a T-cell-based vaccine in rhesus monkeys," Nature, vol. 457, No. 7225, pp. 87-91 (Jan. 2009).

Lore et al, "Myeloid and Plasmacytoid Dendritic Cells are Susceptible to Recombinant Adenovirus Vectors and Stimulate Polyfunctional Memory T Cell Responses," The Joumal of Immunology, vol. 179, No. 3, pp. 1721-1729 (2007).

Mayr et al, " Abstammung, Eigenschaften und Verwendung des attenuierten Vaccina-Stammes MVA," Infection, vol. 3, No. 1, pp. 6-14 (1975).

Mayr et al, "Vaccination Against Pox Diseases Under Immunosuppressive Conditions," Developments in Biological Standardization, vol. 41, pp. 225-234 (1978).

Mayr et al, "The smallpox vaccination strain MVA: marker, genetic structure, experience gained with the parenteral vaccination and behavior in organisms with a debilitated defence mechanisms," Zentralbl Bacteriol (B), vol. 167, pp. 375-390 (1978).

McCoy et al, "Effect of Preexisting Immunity to Adenovirus Human Serotype 5 Antigens on the Immune Responses of Nonhuman Primates to Vaccine Regimens Based on Human- or Chimpanzee-Derived Adenovirus Vectors", Journal of Virology, vol. 81, No. 12, p. 6594-6604, doi:10.1128/JVI.02497-06, Jun. 2007.

(56) References Cited

OTHER PUBLICATIONS

Needleman et al, "A General Method Applicable to the Search Similarities in the Amino Acid Sequence of Two Proteins," Journal of Molecular Biology, vol. 48, pp. 443-453 (1970).
Pearson et al, "Improved tools for biological sequence comparison," Proceedings of the National Academy of Sciences of the United States of America, vol. 85, pp. 2444-2448 (1988).
Peters et al, "Filoviruses as emerging pathogens," Seminars in Virology, vol. 5, pp. 147-154 (1994).
Radosevic et al, "Protective Immune Responses to a Recombinant Adenovirus Type 35 Tuberculosis Vaccine in Two Mouse Strains: CD4 and CD8 T-Cell Epitope Mapping and Role of Gamma Interferon," Infection and Immunity, vol. 75, No. 8, pp. 4105-4115 (Aug. 2007).
Sanchez et al, "The virion glycoproteins of Ebola virus are encoded in two reading frames and are expressed through transcriptional editing," Proceedings of the National Academy of Sciences of the United States of America, vol. 93, pp. 3602-3607 (Apr. 1996).
Shiver et al, "Replication-incompetent adenoviral vaccine vector elicits effective anti-immunodeficiency-virus immunity," Nature, vol. 415, pp. 331-335 (Jan. 2002).
Smith et al, "Comparison of Biosequences," Advances in Applied Mathematics, vol. 2, pp. 482-489 (1981).
Santra et al, "Heterologous prime/boost immunizations of rhesus monkeys using chimpanzee adenovirus vectors," Vaccine, vol. 27, No. 42, pp. 5837-5845 (Sep. 2009).
Stickl et al, "Intracutaneous smallpox vaccination with a weak pathogenic vaccinia virus ('MVA virus')," Munchener medizinische Wochenschrift, vol. 113, pp. 1149-1153 (1971).
Stickl, "Smallpox Vaccination and its Consequences: First Experiences with the Highly Attenuated Smallpox Vaccine "MVA"," Preventive Medicine, vol. 3, pp. 97-101 (1974).
Sullivan et al, "Development of a preventive vaccine for Ebola virus infection in primates," Nature, vol. 408, No. 6812, pp. 605-609 (Nov. 2000).
Sullivan et al, "Accelerated vaccination for Ebola virus haemorrhagic fever in non-human primates," Nature, vol. 424, No. 6949, pp. 681-684 (Nov. 2003).
Roland Zahn et al, "Ad35 and Ad26 Vaccine Vectors Induce Potent and Cross-Reactive Antibody and T-Cell Responses to Multiple Filovirus Species", PLOS ONE, (Dec. 6, 2012), vol. 7, No. 12, doi:10.1371/journal.pone.0044115, p. e44115, XP055159321.
Barouch et al, "Vaccine Protection Against Acquisition of Neutralization-Resistant SIV Challenges in Rhesus Monkeys," Nature, vol. 482, No. 7383, pp. 89-93 (Feb. 2012).
Gilbert et al, "Enhanced CD8 T Cell Imunnogenicity and Protective Efficacy in a Mouse Malaria Model Using a Recombinant Adenoviral Vaccine in Heterologous Prime-Boost Immunisation Regimes," Vaccine, vol. 20, No. 7-8, pp. 1039-1045 (2002).
Roshorm et al, "T Cells Induced by Recombinant Chimpanzee Adenovirus Alone and in Prime-Boost Regimens Decrease Chimeric EcoHIV/NDK Challenge Virus Load," European Jounral of Immunology, vol. 42, No. 12, pp. 3243-3255 (2012).
Subbotina et al, "Genetic Factors of Ebola Virus Virulence in Guinea Pigs," Virus Research, vol. 153, No. 1, pp. 121-133 (2010).
Sanchez et al, "Analysis of Human Peripheral Blood Samples from Fatal and Nonfatal Cases of Ebola (Sudan) Hemorrhagic Fever: Cellular Responses, Virus Load and Nitric Oxide Levels," Jounral of Virology, vol. 78, No. 19, pp. 10370-10377 (2004).
Towner et al, "Marburgvirus Genomics and Association with a Large Hemorrhagic Fever Outbreak in Angola," Jounral of Virology, vol. 80, No. 13, pp. 6497-6516 (2006).
Enterlein et al, "Rescue of Recombinant Marburg Virus from cDNA is Dependent on Nucleocapsid Protein VP30," Jounral of Virology, vol. 80, No. 2, pp. 1038-1043 (2006).
Towner et al, "Newly Discovered Ebola Virus Associated With Hemorrhagic Fever Outbreak in Uganda," PLOS Pathogens Public Library of Science, US, vol. 4, No. 11, pp. 1-6 (2008).
Geisbert et al., Evaluation in Nonhuman Primates of Vaccines against Ebola Virus, Emerging Infectious Disease, 8: 503-507 (2002).
Geisbert et al, "Recombinant Adenovirus Serotype 26 (Ad26) and Ad35 Vaccine Vectors Bypass Immunity to Ad5 and Protect Nonhuman Primates Against Ebolavirus Challenge," Jounral of Virology, vol. 85, No. 9, pp. 4222-4233 (2011).
Wang et al, "De Novo Syntheses of Marburg Virus Antigens From Adenovirus Vectors Induce Potent Humoral and Cellular Immune Response," Vaccine, vol. 24, No. 15, pp. 2975-2986 (2006).
Hill et al., "Prime-boost vectored malaria vaccines: progress and prospects," Human Vaccines, vol. 6, No. 1, pp. 78-83 (2010).
Ophorst et al., "Increased Immunogenicity of Recombinant Ad35-based Malaria Vaccine Through Formulation with Aluminum Phosphate Adjuvant," Vaccine, vol. 25, pp. 6501-10 (2007).
Lee et al, "Recent Advances of Vaccine Adjuvants for Infectious Diseases," Immune Network, vol. 15, No. 2, pp. 51-57 (2015).
Butterfield et al., "Cancer vaccines," BMJ, vol. 350, pp. h988 (2015).
Fenoglio et al, "Generation of more effective cancer vaccines," Hum. Vaccine Immunother., vol. 9, No. 12, pp. 2543-2547 (2013).
Swain et al., "Expanding roles for CD4+ T cells in immunity to viruses," Nat. Rev. Immunol., vol. 12, No. 2, pp. 136-148 (2012).
Sant et al, "Revealing the role of CD4+ T cells in viral immunity," J. Exp. Med., vol. 209, No. 8, pp. 1391-1395 (2012).
Wilkinson et al., "Preexisting influenza-specific CD4+ T cells correlate with disease protection against influenza challenge in humans," Nat. Med., vol. 18, No. 2, pp. 274-280 (2012).
Altenburg et al., "Modified Vaccinia Virus Ankara (MVA) as Production Platform for Vaccines against Influenza and other Viral Respiratory Diseases" Viruses, vol. 6, pp. 2735-2761, 201.
Lu, "Heterologous Prime-Boost Vaccination", Curr Opin Immunol, 21(3), pp. 346-351, Jun. 2009.
Callendret et al, "A prohpylactic multivalent vaccine against filovirus species is immunogenic . . ."PLOS One, 2018, vol. 13, pp. 1-24.
Lauterback et al. Genetic adjubantation of recombinant MVA with CD40L potentiates CD8T cell mediated immunity, Fronteirs in Immunology 4:1-16.
Rimmelzwaan et al., Candidate influenza vaccines based on recombinant modified vaccinia virus Ankara, Expert Review of Vaccines, 8:447-454 (2009).
Keefer et al., A phase 1 trial of preventive HIV vaccination with heterologous poxviral vectors containing matching HIV-1 inserts in healthy HIV-uninfected subjects, Vaccine, 29: 1948-1958 (2011).
Hodge et al., Harnessing the unique local immunostimulatory properties of modified vaccinia Ankara (MVA) virus to generate superior tumor . . ., Vaccine, 27:4475-4482 (2009).
Hutchings et al., Combination of Protein and Viral Vaccines Induces Potent Cellular and Humoral Immune Responses and Enhanced Protection, Infection and Immunity, 75: 5819-5826.
Warfield et al., Advances in Virus-Like Particle Vaccines for Filoviruses, Journal of Infectious Disease, S1053-S1059 (2011).
Ning et al., The role of Ebola virus glycoproteins in viral pathogenesis, Virological Sinica, 32(1):3-15 (2017).
Falzarano et al., Progress in filovirus vaccine development: evaluating the potential for clinical use, Exp. Rev. Vaccines. 10(1):63-77 (2011).
Hoenen et al., Ebola virus: unravelling pathogenesis to combat a deadly disease, Trends Mol. Med. 12(5):20-215 (2006).
Nakayama and Saijo, Animal models for Ebola and Marburg virus infections, Front Microbiol. 4:1-20. (2013).

MARV Angola GP ELISA

| study week: | 0 4 8 10 11 | 0 4 8 10 11 | 0 4 8 10 11 |
|---|---|---|---|
| Week 0: | Ad26.empty | Ad26.Filo | MVA-BN-Filo |
| Week 4: | ∅ | ∅ | ∅ |
| Week 8: | TBS | MVA-BN-Filo | Ad26.Filo |

SEQUENCE LISTING

```
<160> NUMBER OF SEQ ID NOS: 5

<210> SEQ ID NO 1
<211> LENGTH: 676
<212> TYPE: PRT
<213> ORGANISM: Ebola virus Zaire, strain Mayinga

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
```

-continued

```
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605
```

```
Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675


<210> SEQ ID NO 2
<211> LENGTH: 676
<212> TYPE: PRT
<213> ORGANISM: Ebola virus Sudan, strain Gulu

<400> SEQUENCE: 2

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
        275                 280                 285

Ala Phe Trp Glu Asn Lys Lys Asn Leu Ser Glu Gln Leu Arg Gly Glu
```

-continued

```
    290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
        355                 360                 365

Glu Gly Arg Arg Val Gly Val Asn Thr Gln Glu Thr Ile Thr Glu Thr
    370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Ser Pro Thr
                405                 410                 415

Thr Ala Pro Ser Pro Glu Ala Gln Thr Pro Thr Thr His Thr Ser Gly
            420                 425                 430

Pro Ser Val Met Ala Thr Glu Glu Pro Thr Thr Pro Pro Gly Ser Ser
        435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675
```

```
<210> SEQ ID NO 3
<211> LENGTH: 681
<212> TYPE: PRT
<213> ORGANISM: Marburg virus Angola
```

-continued

<400> SEQUENCE: 3

```
Met Lys Thr Thr Cys Leu Leu Ile Ser Leu Ile Leu Ile Gln Gly Val
1               5                   10                  15

Lys Thr Leu Pro Ile Leu Glu Ile Ala Ser Asn Ile Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Ala Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Lys Pro Leu Pro Leu Pro Thr Ala His Pro
225                 230                 235                 240

Glu Val Lys Leu Thr Ser Thr Ser Thr Asp Ala Thr Lys Leu Asn Thr
                245                 250                 255

Thr Asp Pro Asn Ser Asp Asp Glu Asp Leu Thr Thr Ser Gly Ser Gly
            260                 265                 270

Ser Gly Glu Gln Glu Pro Tyr Thr Thr Ser Asp Ala Ala Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Gly Val Val Thr
305                 310                 315                 320

Glu Pro Gly Lys Thr Asn Thr Thr Ala Gln Pro Ser Met Pro Pro His
                325                 330                 335

Asn Thr Thr Thr Ile Ser Thr Asn Asn Thr Ser Lys His Asn Leu Ser
            340                 345                 350

Thr Pro Ser Val Pro Ile Gln Asn Ala Thr Asn Tyr Asn Thr Gln Ser
        355                 360                 365

Thr Ala Pro Glu Asn Glu Gln Thr Ser Ala Pro Ser Lys Thr Thr Leu
    370                 375                 380

Leu Pro Thr Glu Asn Pro Thr Thr Ala Lys Ser Thr Asn Ser Thr Lys
385                 390                 395                 400

Ser Pro Thr Thr Thr Val Pro Asn Thr Thr Asn Lys Tyr Ser Thr Ser
```

-continued

```
                405                 410                 415

Pro Ser Pro Thr Pro Asn Ser Thr Ala Gln His Leu Val Tyr Phe Arg
            420                 425                 430

Arg Lys Arg Asn Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Lys Val Asn Glu Asn Thr Ala His Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Ala Arg Trp Gly Gly Thr Cys Lys Val Leu Gly Pro Asp
        595                 600                 605

Cys Cys Ile Gly Ile Glu Asp Leu Ser Arg Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680


<210> SEQ ID NO 4
<211> LENGTH: 681
<212> TYPE: PRT
<213> ORGANISM: Marburg virus Musoke

<400> SEQUENCE: 4

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95
```

-continued

```
Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Ala Leu Gln Glu Tyr Asn Ser Thr Lys Asn Gln
    210                 215                 220

Thr Cys Ala Pro Ser Lys Ile Pro Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
            340                 345                 350

Thr Leu Ser Ala Pro Leu Gln Asn Thr Thr Asn Asp Asn Thr Gln Ser
        355                 360                 365

Thr Ile Thr Glu Asn Glu Gln Thr Ser Ala Pro Ser Ile Thr Thr Leu
    370                 375                 380

Pro Pro Thr Gly Asn Pro Thr Thr Ala Lys Ser Thr Ser Ser Lys Lys
385                 390                 395                 400

Gly Pro Ala Thr Thr Ala Pro Asn Thr Thr Asn Glu His Phe Thr Ser
                405                 410                 415

Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
```

```
        515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680


<210> SEQ ID NO 5
<211> LENGTH: 739
<212> TYPE: PRT
<213> ORGANISM: Ebola virus Tai Forest / Ivory coast

<400> SEQUENCE: 5

Met Glu Ser Arg Ala His Lys Ala Trp Met Thr His Thr Ala Ser Gly
1               5                   10                  15

Phe Glu Thr Asp Tyr His Lys Ile Leu Thr Ala Gly Leu Ser Val Gln
            20                  25                  30

Gln Gly Ile Val Arg Gln Arg Val Ile Gln Val His Gln Val Thr Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Gln Phe Leu Glu Ser Asn Ala Val
                85                  90                  95

Lys Tyr Leu Glu Gly His Gly Phe Arg Phe Glu Val Arg Lys Lys Glu
            100                 105                 110

Gly Val Lys Arg Leu Glu Glu Leu Leu Pro Ala Ala Ser Ser Gly Lys
        115                 120                 125

Ser Ile Arg Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ser Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205
```

-continued

```
Leu Ile Lys Phe Leu Leu Ile His Gln Gly Met His Met Val Ala Gly
    210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu His Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Gln His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Lys Tyr Ala Glu Ser Arg Glu Leu Asp His Leu Gly Leu
        355                 360                 365

Asp Asp Gln Glu Lys Lys Ile Leu Lys Asp Phe His Gln Lys Lys Asn
    370                 375                 380

Glu Ile Ser Phe Gln Gln Thr Thr Ala Met Val Thr Leu Arg Lys Glu
385                 390                 395                 400

Arg Leu Ala Lys Leu Thr Glu Ala Ile Thr Ser Thr Ser Leu Leu Lys
                405                 410                 415

Thr Gly Lys Gln Tyr Asp Asp Asp Asn Asp Ile Pro Phe Pro Gly Pro
            420                 425                 430

Ile Asn Asp Asn Glu Asn Ser Glu Gln Gln Asp Asp Asp Pro Thr Asp
        435                 440                 445

Ser Gln Asp Thr Thr Ile Pro Asp Ile Ile Val Asp Pro Asp Asp Gly
    450                 455                 460

Arg Tyr Asn Asn Tyr Gly Asp Tyr Pro Ser Glu Thr Ala Asn Ala Pro
465                 470                 475                 480

Glu Asp Leu Val Leu Phe Asp Leu Glu Asp Gly Asp Glu Asp Asp His
                485                 490                 495

Arg Pro Ser Ser Ser Ser Glu Asn Asn Asn Lys His Ser Leu Thr Gly
            500                 505                 510

Thr Asp Ser Asn Lys Thr Ser Asn Trp Asn Arg Asn Pro Thr Asn Met
        515                 520                 525

Pro Lys Lys Asp Ser Thr Gln Asn Asn Asp Asn Pro Ala Gln Arg Ala
    530                 535                 540

Gln Glu Tyr Ala Arg Asp Asn Ile Gln Asp Thr Pro Thr Pro His Arg
545                 550                 555                 560

Ala Leu Thr Pro Ile Ser Glu Glu Thr Gly Ser Asn Gly His Asn Glu
                565                 570                 575

Asp Asp Ile Asp Ser Ile Pro Pro Leu Glu Ser Asp Glu Glu Asn Asn
            580                 585                 590

Thr Glu Thr Thr Ile Thr Thr Thr Lys Asn Thr Thr Ala Pro Pro Ala
        595                 600                 605

Pro Val Tyr Arg Ser Asn Ser Glu Lys Glu Pro Leu Pro Gln Glu Lys
    610                 615                 620

Ser Gln Lys Gln Pro Asn Gln Val Ser Gly Ser Glu Asn Thr Asp Asn
```

-continued

```
625                 630                 635                 640

Lys Pro His Ser Glu Gln Ser Val Glu Glu Met Tyr Arg His Ile Leu
                645                 650                 655

Gln Thr Gln Gly Pro Phe Asp Ala Ile Leu Tyr Tyr Tyr Met Met Thr
            660                 665                 670

Glu Glu Pro Ile Val Phe Ser Thr Ser Asp Gly Lys Glu Tyr Val Tyr
        675                 680                 685

Pro Asp Ser Leu Glu Gly Glu His Pro Pro Trp Leu Ser Glu Lys Glu
    690                 695                 700

Ala Leu Asn Glu Asp Asn Arg Phe Ile Thr Met Asp Asp Gln Gln Phe
705                 710                 715                 720

Tyr Trp Pro Val Met Asn His Arg Asn Lys Phe Met Ala Ile Leu Gln
                725                 730                 735

His His Lys
```

METHODS AND COMPOSITIONS FOR INDUCING PROTECTIVE IMMUNITY AGAINST A MARBURG VIRUS INFECTION

CROSS-REFERENCE TO RELATED APPLICATION

This application is a Section 371 of International Application No. PCT/IB2017/054286, filed Jul. 14, 2017, which was published in the English language on Jan. 18, 2018 under International Publication No. WO 2018/011768 A1, which claims the benefit of U.S. Provisional Application No. 62/362,831, filed Jul. 15, 2016, and the disclosures of which are incorporated herein by reference.

STATEMENT OF GOVERNMENT SUPPORT

This invention was made with government support under contract HHSN272200800056C, awarded by the National Institute of Health. The government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_135U1", creation date of Jan. 11, 2019, and having a size of about 30 KB. The sequence listing submitted via EFS-Web is part of the specification and is herein incorporated by reference in its entirety.

FIELD OF THE INVENTION

This invention relates to compositions, vaccines and methods for inducing protective immunity against a Marburg virus infection.

BACKGROUND OF THE INVENTION

Ebolaviruses, such as Zaire ebolavirus (EBOV) and Sudan ebolavirus (SUDV), and the closely related Marburg virus (MARV), are associated with outbreaks of highly lethal Hemorrhagic Fever (HF) in humans and primates, mainly located in Africa with occasional spillover in North America and Europe. These viruses are filoviruses that are known to infect humans and non-human primates with severe health consequences, including death. Filovirus infections have resulted in case fatality rates of up to 90% in humans. EBOV, SUDV, and MARV infections cause HF with death often occurring within 7 to 10 days post-infection. HF presents as an acute febrile syndrome manifested by an abrupt fever, nausea, vomiting, diarrhea, maculopapular rash, malaise, prostration, generalized signs of increased vascular permeability, coagulation abnormalities, and dysregulation of the innate immune response. Much of the disease appears to be caused by dysregulation of innate immune responses to the infection and by replication of virus in vascular endothelial cells, which induces death of host cells and destruction of the endothelial barrier. Filoviruses can be spread by small particle aerosol or by direct contact with infected blood, organs, and body fluids of human or NHP origin. Infection with a single virion is reported to be sufficient to cause HF in humans. Presently, there is no therapeutic or vaccine approved for treatment or prevention of HF. Supportive care remains the only approved medical intervention for individuals who become infected with filoviruses.

As the cause of severe human disease, filoviruses continue to be of concern as both a source of natural infections, and also as possible agents of bioterrorism. The reservoir for filoviruses in the wild has not yet been definitively identified. Four subtypes of Ebolaviruses have been described to cause HF, i.e., those in the Zaire, Sudan, Bundibugyo and Ivory Coast episodes (Sanchez, A. et al. 1996 PNAS USA 93:3602-3607). These subtypes of Ebolaviruses have similar genetic organizations, e.g., negative-stranded RNA viruses containing seven linearly arrayed genes. The structural gene products of Ebolaviruses include, for example, the envelope glycoprotein that exists in two alternative forms, a secreted soluble glycoprotein (ssGP) and a transmembrane glycoprotein (GP) generated by RNA editing that mediates viral entry (Sanchez, et al. 1996 PNAS USA 93:3602-3607).

Marburg virus (MARV) causes Marburg virus disease (MVD), also referred to as Marburg hemorrhagic fever (MHF), in humans and nonhuman primates. The disease names are derived from the German city Marburg, where MARV was first discovered in an outbreak in 1967. Comparative analyses of the GP and viral protein (VP) 35 genes of MARV strains showed that there are two distinct lineages within the *Marburg marburgvirus* species of MARV, the Marburg lineage and Ravn lineage. There are a number of isolated strains of the Marburg lineage, such as the original MARV isolates from the 1967 episodes in Marburg (Popp and Ratayczak strains), the Ozolin strain from a case in 1975 in South Africa, the Musoke strain (MARV-Musoke) from a 1980 case in Kenya, and a seemingly more pathogenic Angola strain (MARV-Angola). The Ravn lineage includes an isolate from Kenya in 1987 (Ravn strain). See Daddario-DiCaprio et al., *J. of Virology*, October 2006, p. 9659-9666. The structural proteins of MARV include four proteins (NP, VP35, VP30, and L) that make up the helical nucleocapsid, which is surrounded by a matrix that is composed of the viral proteins VP40 and VP24. The surface of MARV virions is coated with spikes that consist of the structural glycoprotein (GP). The MARV GP plays a role in virus entry and pathogenesis and serves as a major and logical target for vaccine strategies. Id.

It has been suggested that immunization can be useful in protecting against filovirus infection because there appears to be less nucleotide polymorphism within filovirus subtypes than among other RNA viruses (Sanchez et al. 1996 PNAS USA 93:3602-3607). Until recently, developments of preventive vaccines against filoviruses have had variable results, partly because the requirements for protective immune responses against filovirus infections are poorly understood. Additionally, the large number of filoviruses circulating within natural reservoirs complicates efforts to design a vaccine that protects against all species of filoviruses.

Currently, there are several vaccine antigen delivery platforms that demonstrated various levels of protection in non-human primates (NHPs) exposed with high infectious doses of filoviruses. Vaccine candidates are in development based on a variety of platform technologies including replication competent vectors (e.g. Vesicular Stomatitis Virus; Rabies virus; Parainfluenza Virus); replication incompetent vectors (Adenovirus, Modified Vaccinia Ankara Virus); protein subunits inclusive of Virus Like Particles expressed in bacterial cells, insect cells, mammalian cells, plant cells; DNA vaccines; and/or live and killed attenuated filovirus (Friedrich et al., 2012). The EBOV glycoprotein GP is an essential component of a vaccine that protects against exposures with the same species of EBOV. Furthermore, inclusion of the GP from EBOV and SUDV, the two most virulent species of ebolaviruses, can protect monkeys against EBOV and SUDV intramuscular exposures, as well as exposures with the distantly related Bundibugyo (BDBV), Taï Forest ebolavirus (TAFV; formerly known as Ivory Coast or Cote d'Ivoire) species. Likewise, inclusion of the GP from MARV can protect monkeys against MARV intramuscular and aerosol exposures. The development of medical countermeasures for these viruses is a high priority, in particular the development of a PAN-filovirus vaccine—that is one vaccine that protects against all pathogenic filoviruses.

Replication-defective adenovirus vectors (rAd) are powerful inducers of cellular immune responses and have therefore come to serve as useful vectors for gene-based vaccines particularly for lentiviruses and filoviruses, as well as other nonviral pathogens (Shiver, et al., (2002) Nature 415(6869): 331-5; (Hill, et al., Hum Vaccin 6(1): 78-83; Sullivan, et al., (2000) Nature 408(6812): 605-9; Sullivan et al., (2003) Nature 424(6949): 681-4; Sullivan, et al., (2006) PLoS Med 3(6): e177; Radosevic, et al., (2007); Santra, et al., (2009) Vaccine 27(42): 5837-45.

Adenovirus-based vaccines have several advantages as human vaccines since they can be produced to high titers under GMP conditions and have proven to be safe and immunogenic in humans (Asmuth, et al., J Infect Dis 201(1): 132-41; Kibuuka, et al., J Infect Dis 201(4): 600-7; Koup, et al., PLoS One 5(2): e9015; Catanzaro, et al., (2006) J Infect Dis 194(12): 1638-49; Harro, et al., (2009) Clin Vaccine Immunol 16(9): 1285-92). While most of the initial vaccine work was conducted using rAd5 due to its significant potency in eliciting broad antibody and CD8+ T cell responses, pre-existing immunity to rAd5 in humans may limit efficacy (Catanzaro, (2006); Cheng, et al., (2007) PLoS Pathog 3(2): e25; McCoy, et al., (2007) J Virol 81(12): 6594-604; Buchbinder, et al., (2008) Lancet 372(9653): 1881-93). This property might restrict the use of rAd5 in clinical applications for many vaccines that are currently in development including Ebolavirus (EBOV) and Marburg virus (MARV).

Replication-defective adenovirus vectors, rAd26 and rAd35, derived from adenovirus serotype 26 and serotype 35, respectively, have the ability to circumvent Ad5 pre-existing immunity. rAd26 can be grown to high titers in Ad5 E1-complementing cell lines suitable for manufacturing these vectors at a large scale and at clinical grade (Abbink, et al., 2007, Virol 81(9): 4654-63), and this vector has been shown to induce humoral and cell-mediated immune responses in prime-boost vaccine strategies (Abbink, et al., 2007, supra; Liu, et al., (2009) Nature 457(7225): 87-91). rAd35 vectors grow to high titers on cell lines suitable for production of clinical-grade vaccines (Havenga, et al., (2006) J Gen Virol 87(Pt 8): 2135-43), and have been formulated for injection as well as stable inhalable powder (Jin, et al., Vaccine 28(27): 4369-75). These vectors show efficient transduction of human dendritic cells (de Gruijl, et al., (2006) J Immunol 177(4): 2208-15; Lore, et al., (2007) J Immunol 179(3): 1721-9), and thus have the capability to mediate high level antigen delivery and presentation.

Modified Vaccinia Ankara (MVA) virus is related to Vaccinia virus, a member of the genera Orthopoxvirus in the family of Poxviridae. Poxviruses are known to be good inducers of CD8 T cell responses because of their intracytoplasmic expression. However, they are generally believed to be poor at generating CD4 MHC class II restricted T cells (see for example Haslett et al. Journal of Infectious Diseases 181: 1264-72 (2000), page 1268). MVA has been engineered for use as a viral vector for recombinant gene expression or as recombinant vaccine.

Strains of MVA having enhanced safety profiles for the development of safer products, such as vaccines or pharmaceuticals, have been developed by Bavarian Nordic. MVA was further passaged by Bavarian Nordic and is designated MVA-BN, a representative sample of which was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

MVA-BN can attach to and enter human cells where virally-encoded genes are expressed very efficiently. MVA-BN is replication incompetent, meaning that the virus does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome (E. Harrer et al. (2005), Antivir. Ther. 10(2):285-300; A. Cosma et al. (2003), Vaccine 22(1):21-9; M. Di Nicola et al. (2003), Hum. Gene Ther. 14(14):1347-1360; M. Di Nicola et al. (2004), Clin. Cancer Res., 10(16):5381-5390).

There is an unmet need for improved vaccines that elicit immune responses against Marburg viruses.

BRIEF SUMMARY OF THE INVENTION

It is discovered in the present invention that various prime-boost combinations of replication incompetent vectors generate effective immune protection against Marburg virus infections.

Accordingly, one general aspect of the present invention relates to a combination vaccine comprising:

(i) a first composition comprising an immunologically effective amount of an adenovirus vector comprising a nucleic acid encoding a first antigenic protein of a Marburg virus, together with a pharmaceutically acceptable carrier; and (ii) a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, together with a pharmaceutically acceptable carrier;

wherein the first antigenic protein and the second antigenic protein share at least one antigenic determinant, and one of the compositions is a priming composition and the other composition is a boosting composition. Preferably, the first composition is the priming composition and the second composition is the boosting composition, and more preferably, the boosting composition is to be administered 1-12 weeks after the priming composition.

Another general aspect of the present invention relates to the use of:

a first composition comprising an immunologically effective amount of an adenovirus vector comprising a nucleic acid encoding a first antigenic protein of a Marburg virus; and a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, for generating a protective immune response against a Marburg virus; wherein the first and second compositions are used for priming and for boosting said immune response, respectively, or vice versa, and the first antigenic protein and the second antigenic protein share at least one antigenic determinant. Preferably, the first composition is used for priming and the second composition is used for boosting, and more preferably, the boosting composition is administered 1-12 weeks after the priming composition.

The Marburg virus according to the present invention can be any isolate or strain of the *Marburg marburgvirus* species, including but not limited to, the Marburg Popp strain, Ratayczak strain, Ozolin strain, Musoke strain (MARV-Musoke), Angola strain (MARV-Angola), and the Ravn strain.

The antigenic proteins can be any protein comprising an antigenic determinant. In a preferred embodiment the antigenic proteins include Marburg virus glycoproteins (GPs) or nucleoproteins (NPs), and the antigenic proteins can further be one or more antigenic protein from at least one additional filovirus, such as Ebola. Other antigenic proteins, such as an NP, VP35, VP30, L, VP40, VP24 or GP of a Marburg virus, can also be used in the invention. The antigenic proteins encoded by the adenovirus vectors or MVA vectors comprised in the first and second composition according to embodiments of the present invention can include any antigenic protein from any isolate of Marburg virus, preferably, GPs of at least one of MARV-Musoke and MARV-Angola.

In a preferred embodiment, the adenovirus vector in the first composition (i) comprises a nucleic acid encoding a first antigenic protein of a Marburg virus having the amino acid sequence of SEQ ID NO:3, and the MVA vector in the second composition (ii) comprises a nucleic acid encoding a second antigenic protein of a Marburg virus having the amino acid sequence of SEQ ID NO:3 or SEQ ID NO:4.

In yet another preferred embodiment, the MVA vector in the second composition (ii) comprises a nucleic acid encoding antigenic proteins of at least four filovirus subtypes. Preferably said MVA vector comprises a nucleic acid encoding antigenic proteins from four different filovirus subtypes, and the antigenic proteins having the amino acid sequences of SEQ ID NO: 1, SEQ ID NO: 2, SEQ ID NO: 4, and SEQ ID NO: 5, respectively.

In a preferred embodiment, the adenovirus vectors used in the first composition is a rAd26 vector. It is contemplated that the methods, vaccines, and compositions described herein can be embodied in a kit. For example, in one embodiment, the present invention can include a kit comprising:

(i) a first composition comprising an immunologically effective amount of an adenovirus vector comprising a nucleic acid encoding a first antigenic protein of a Marburg virus, together with a pharmaceutically acceptable carrier; and (ii) a second composition comprising an immunologically effective amount of an MVA vector comprising a nucleic acid encoding a second antigenic protein of a Marburg virus, preferably the nucleic acid further encoding one or more antigenic proteins of one or more additional filovirus subtypes, together with a pharmaceutically acceptable carrier;

wherein the first antigenic protein and the second antigenic protein share at least one antigenic determinant, and one of the compositions is a priming composition and the other composition is a boosting composition. Preferably, the first composition is the priming composition and the second composition is the boosting composition, and more preferably, the boosting composition is to be administered 1-12 weeks after the priming composition.

Therefore in a preferred embodiment, the present invention relates to a combination vaccine, a kit or a use wherein the adenovirus vector in composition (i) comprises a nucleic acid encoding a first antigenic protein having the amino acid sequence of SEQ ID NO: 3; and wherein the MVA vector in composition (ii) comprises a nucleic acid encoding antigenic proteins from four different filovirus subtypes and the antigenic proteins having the amino acid sequences of SEQ ID NO: 1, SEQ ID NO: 2, SEQ ID NO: 4, and SEQ ID NO: 5, respectively.

In a preferred embodiment, the adenovirus vectors comprised in the combination vaccine, kit of the present invention, or the adenovirus vectors used for generating a protective immune response against at least one Marburg virus are rAd26 or rAd35 vectors. In a preferred embodiment said adenovirus vectors are rAd26 vectors. In a preferred embodiment of this use, the boosting composition is administered 1-12 weeks after the administration of the priming composition.

One additional general aspect of the present invention relates to a method of inducing an immune response against a Marburg virus in a subject, the method comprising:

a. administering to the subject a first composition comprising an immunologically effective amount of an adenovirus vector comprising a nucleic acid encoding a first antigenic glycoprotein of a Marburg virus; and b. administering to the subject a second composition comprising an immunologically effective amount of an MVA vector comprising a nucleic acid encoding a second antigenic protein of a Marburg virus, preferably the nucleic acid further encoding one or more antigenic proteins of one or more additional filovirus subtypes;

wherein steps (a) and (b) are conducted in either order, and the first antigenic protein and the second antigenic protein share at least one antigenic determinant.

In another embodiment, the adenovirus vector in the first composition comprises a nucleic acid encoding a first antigenic protein having the amino acid sequence of SEQ ID NO:3, and the MVA vector in the second composition comprises a nucleic acid encoding a second antigenic protein having the amino acid sequence of SEQ ID NO:3 or SEQ ID NO:4.

In an even more preferred embodiment, the MVA vector in the second composition comprises a nucleic acid encoding antigenic proteins of at least four filovirus subtypes. Preferably said MVA vector comprises a nucleic acid encoding antigenic proteins from four different filovirus subtypes, and the antigenic proteins have the amino acid sequences of SEQ ID NO: 1, SEQ ID NO: 2, SEQ ID NO: 4, and SEQ ID NO: 5, respectively.

Therefore, in a preferred embodiment, the present invention relates to method of inducing an immune response against a Marburg virus in a subject, wherein the adenovirus vector in the first composition comprises a nucleic acid encoding an antigenic protein having the amino acid sequence of SEQ ID NO: 3; and wherein the MVA vector in the second composition comprises a nucleic acid encoding antigenic proteins from four different filovirus subtypes and the antigenic proteins have the amino acid sequences of SEQ ID NO: 1, SEQ ID NO: 2, SEQ ID NO: 4, and SEQ ID NO: 5, respectively.

In a preferred embodiment, the adenovirus vectors used in the method of the present invention are rAd26 or rAd35 vectors.

In another preferred embodiment of the present invention, step (a) and step (b) of the method are conducted 1-12 weeks apart. One of the steps (a) and (b) is conducted for priming vaccination and the other step for boosting vaccination.

In another preferred embodiment, the priming vaccination step (a) is conducted at week 0, followed by the boosting vaccination step (b) at week 1-10, more preferably at week 6-10 and even more preferably at week 8. In another preferred embodiment, the priming vaccination step (a) is conducted at week 0, followed by the boosting vaccination step (b) at week 1-4, preferably at week 1, 2 or 4.

In another preferred embodiment, the priming vaccination step (b) is conducted at week 0, followed by the boosting vaccination step (a) at week 1-10, more preferably at week 6-10 and even more preferably at week 8. In another preferred embodiment, the priming vaccination step (b) is conducted at week 0, followed by the boosting vaccination step (a) at week 1-4, preferably at week 1, 2 or 4.

In a preferred embodiment of the present invention, the method comprises a priming vaccination with an immunologically effective amount of an rAd26 vector expressing a first Marburg virus antigenic protein, followed by a boosting vaccination with an immunologically effective amount of one or more vectors different from rAd26, preferably MVA vectors, expressing a second Marburg virus antigenic protein that shares at least one antigenic determinant with the first Marburg virus antigenic protein, preferably further expressing one or more antigenic proteins from one or more additional filovirus subtypes or substantially similar glycoproteins. The first and second Marburg virus antigenic proteins can be identical or different.

In preferred embodiments of the present invention, the one or more filoviruses are Ebolaviruses or Marburgviruses. The Ebolavirus can be of any species or isolates, for example, Zaire ebolavirus (EBOV) and Sudan ebolavirus (SUDV), Reston, Bundibugyo, Taï Forest. The Marburg virus (MARV) may be of any species. The Marburgviruses can be any isolate or strain of the *Marburg marburgvirus* species, including but not limited to, the Marburg Popp strain, Ratayczak strain, Ozolin strain, Musoke strain (MARV-Musoke), and Angola strain (MARV-Angola), and the Ravn strain. Exemplary amino acid sequences of suitable filovirus antigenic proteins include, but are not limited to, SEQ ID NO: 1 to SEQ ID NO: 5.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1:
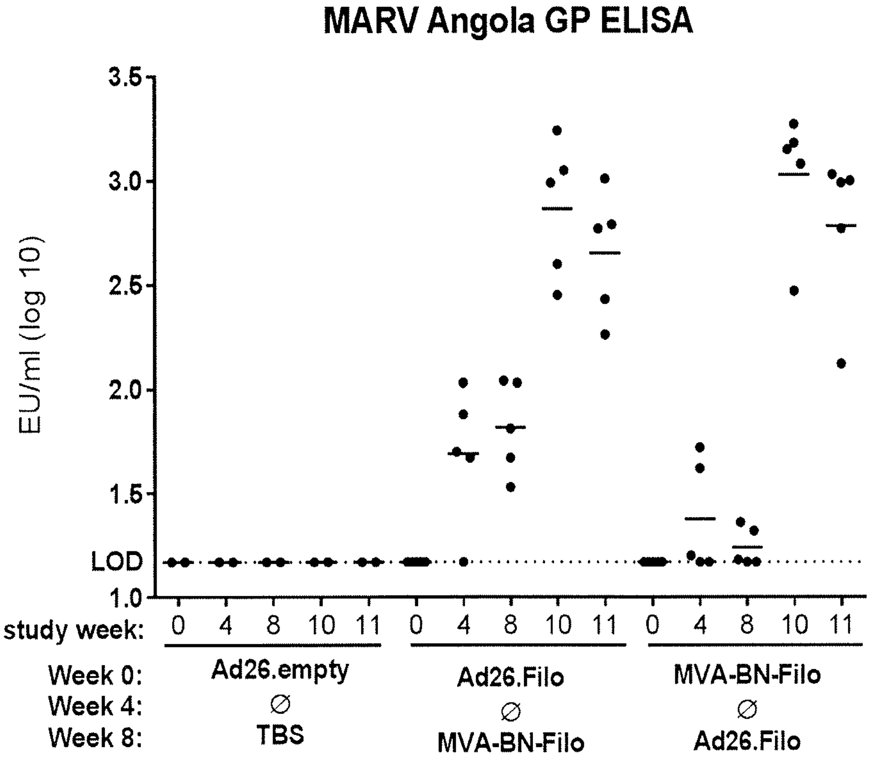
FIG. 1 shows the amount of MARV GP-binding antibodies in serum samples taken from Cynomolgus macaques (*Macaca fascicularis*) (NHPs) vaccinated with different vaccine combinations as analyzed by a MARV GP-specific Enzyme-Linked Immunosorbent Assay (ELISA): log 10-transformed ELISA concentrations (ELISA Units per ml, EU/ml) are shown, and the symbols represent the titers from the individual animals tested, bars represent the mean per group, and dotted line represents the Limit of Detection (LOD) of the assay.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention can be substituted with the term "consisting of", though less preferred.

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

An "adenovirus capsid protein" refers to a protein on the capsid of an adenovirus (e.g., Ad 26 or Ad 35) that is involved in determining the serotype and/or tropism of a particular adenovirus. Adenoviral capsid proteins typically include the fiber, penton and/or hexon proteins. As used herein a "Ad26 capsid protein" or a "Ad35 capsid protein" can be, for example, a chimeric capsid protein that includes at least a part of an Ad26 or Ad35 capsid protein. In certain embodiments, the capsid protein is an entire capsid protein of Ad26 or of Ad35. In certain embodiments, the hexon, penton and fiber are of Ad26 or of Ad35.

The terms "adjuvant" and "immune stimulant" are used interchangeably herein, and are defined as one or more substances that cause stimulation of the immune system. In this context, an adjuvant is used to enhance an immune response to the adenovirus and/or MVA vectors of the invention.

The term "corresponding to", when applied to positions of amino acid residues in sequences, means corresponding positions in a plurality of sequences when the sequences are optimally aligned.

The terms "identical" or percent "identity," in the context of two or more nucleic acids or polypeptide sequences, (e.g., glycoproteins of filovirus and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "substantially similar" in the context of the filovirus antigenic proteins of the invention indicates that a polypeptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

It is discovered in the present invention that heterologous prime-boost combinations, in particular, Ad26 priming followed by MVA boosting and vice versa, are surprisingly effective in generating protective immune responses against one or more subtypes of Marburg viruses.

Filovirus Antigenic Proteins

The Ebola viruses, and the genetically-related Marburg virus, are filoviruses associated with outbreaks of highly lethal hemorrhagic fever in humans and primates in North America, Europe, and Africa (Peters, C. J. et al. in: Fields Virology, eds. Fields, B. N. et al. 1161-1176, Philadelphia, Lippincott-Raven, 1996; Peters, C. J. et al. 1994 Semin Virol 5:147-154). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein (sGP) and a 130 kDa transmembrane glycoprotein (GP) generated by RNA editing that mediates viral entry (Peters, C. J. et al. in: Fields Virology, eds. Fields, B. N. et al. 1161-1176, Philadelphia, Lippincott-Raven, 1996; Sanchez, A. et al. 1996 PNAS USA 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: Fields Virology, eds. Fields, B. N. et al. 1161-1176, Philadelphia, Lippincott-Raven, 1996).

The nucleic acid molecules comprised in the adenovirus and MVA vectors can encode structural gene products of any filovirus species, such as subtypes of Zaire (type species, also referred to herein as ZEBOV), Sudan (also referred to herein as SEBOV), Reston, Bundibugyo, and Ivory Coast. There is a single species of Marburgvirus (also referred to herein as MARV) comprising two genetic lineages, the Marburg lineage and Ravn lineage. The Marburg virus according to the present invention can be any isolate or strain of the *Marburg marburgvirus* species, including but not limited to, the Marburg Popp strain, Ratayczak strain, Ozolin strain, Musoke strain (MARV-Musoke), and Angola strain (MARV-Angola), and the Ravn strain. Preferably, the Marburg virus is at least one of MARV-Musoke and MARV-Angola.

The adenoviral vectors and MVA vectors of the invention can be used to express antigenic proteins which are proteins comprising an antigenic determinant of a wide variety of filovirus antigens. In a typical and preferred embodiment, the vectors of the invention include nucleic acid encoding the transmembrane form of the viral glycoprotein (GP). In other embodiments, the vectors of the invention can encode the secreted form of the viral glycoprotein (ssGP), or the viral nucleoprotein (NP).

One of skill will recognize that the nucleic acid molecules encoding the filovirus antigenic protein can be modified, e.g., the nucleic acid molecules set forth herein can be mutated, as long as the modified expressed protein elicits an immune response against a pathogen or disease. Thus, as used herein, the term "antigenic protein" or "filovirus protein" refers to a protein that comprises at least one antigenic determinant of a filovirus protein described above. The term encompasses filovirus glycoproteins (i.e., gene products of a filovirus) or filovirus nucleoprotein as well as recombinant proteins that comprise one or more filovirus glycoprotein determinants. The term antigenic proteins also encompasses antigenic proteins that are substantially similar to the naturally occurring antigenic proteins. For example, as used herein, a GP of a filovirus, such as a GP of a Marburg virus, can be the naturally occurring GP. A GP of a filovirus can also be a protein that is substantially similar to a naturally occurring GP of a filovirus and contains at least one antigenic determinant of the naturally occurring GP.

In some embodiments, the protein can be mutated so that it is less toxic to cells (see e.g., WO/2006/037038) or can be expressed with increased or decreased level in the cells. The present invention also includes vaccines comprising a combination of nucleic acid molecules. For example, and without limitation, nucleic acid molecules encoding GP, ssGP and NP of the Zaire, Sudan, Marburg and Ivory Coast/TO forest Ebola strains can be combined in any combination, in one vaccine composition.

Adenoviruses

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the present invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50.

According to a particularly preferred embodiment of the invention, an adenovirus is a human adenovirus of one of the serotypes 26 or 35.

An advantage of these serotypes is a low seroprevalence and/or low pre-existing neutralizing antibody titers in the human population. Preparation of rAd26 vectors is described, for example, in WO 2007/104792 and in Abbink et al., (2007) Virol 81(9): 4654-63, both of which are incorporated by reference herein in their entirety. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) J Virol 77(15): 8263-71, all of which are incorporated by reference herein in their entirety. Exemplary genome sequences of Ad35 are found in GenBank Accession AC 000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, J Virol 75: 11603-13; Cohen et al, 2002, Gen Virol 83: 151-55; Kobinger et al, 2006, Virology 346: 394-401; Tatsis et al., 2007, Molecular Therapy 15: 608-17; see also review by Bangari and Mittal, 2006, Vaccine 24: 849-62; and review by Lasaro and Ertl, 2009, Mol Ther 17: 1333-39). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Adenoviral Vectors rAd26 and rAd35

In a preferred embodiment according to the present invention the adenoviral vectors comprise capsid proteins from two rare serotypes: Ad26 and Ad35. In the typical embodiment, the vector is an rAd26 or rAd35 virus.

Thus, the vectors that can be used in the invention comprise an Ad26 or Ad35 capsid protein (e.g., a fiber, penton or hexon protein). One of skill will recognize that it is not necessary that an entire Ad26 or Ad35 capsid protein be used in the vectors of the invention. Thus, chimeric capsid proteins that include at least a part of an Ad26 or Ad35 capsid protein can be used in the vectors of the invention. The vectors of the invention can also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of the Ad26 and Ad35 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad35 or from Ad26 (i.e., the vector is rAd35 or rAd26). In some embodiments, the adenovirus is replication deficient, e.g. because it contains a deletion in the E1 region of the genome. For the adenoviruses of the invention, being derived from Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga et al, 2006, J Gen Virol 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al, 2006, supra; WO 2004/001032).

The preparation of recombinant adenoviral vectors is well known in the art. Preparation of rAd26 vectors is described, for example, in WO 2007/104792 and in Abbink et al., (2007) Virol 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) J Virol 77(15): 8263-71. An exemplary genome sequence of Ad35 is found in GenBank Accession AC_000019.

In an embodiment of the present invention, the vectors useful for the present invention include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention can contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of filovirus glycoproteins can be expressed in the vectors. If required, the heterologous gene encoding the filovirus glycoproteins can be codon-optimized to ensure proper expression in the treated host (e.g., human). Codon-optimization is a technology widely applied in the art. Typically, the heterologous gene is cloned into the E1 and/or the E3 region of the adenoviral genome.

The heterologous filovirus gene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

In a preferred embodiment of the present invention, the rAd vector comprises the GP of a Marburg virus (MARV) or GPs substantially similar thereto.

MVA Vectors

MVA vectors useful for the present invention utilize attenuated virus derived from Modified Vaccinia Ankara virus which is characterized by the loss of their capabilities to reproductively replicate in human cell lines. The MVA vectors express a wide variety of filovirus glycoproteins as well as other structural filovirus proteins, such as VP40 and nucleoprotein (NP).

In one aspect, the present invention provides a recombinant modified vaccinia virus Ankara (MVA) comprising a nucleotide sequence encoding an antigenic determinant of a filovirus glycoprotein (GP), in particular an envelope glycoprotein. In another aspect, the present invention provides a recombinant MVA vector comprising a heterologous nucleotide sequence encoding an antigenic determinant of a filovirus glycoprotein, in particular an envelope glycoprotein, and a heterologous nucleotide sequence encoding an antigenic determinant of a further filovirus protein.

MVA has been generated by more than 570 serial passages on chicken embryo fibroblasts of the dermal vaccinia strain Ankara (Chorioallantois vaccinia virus Ankara virus, CVA; for review see Mayr et al. (1975), Infection 3, 6-14) that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells (Mayr et al. (1975), Infection 3, 6-14). It was shown in a variety of animal models that the resulting MVA was avirulent (Mayr, A. & Danner, K. (1978), Dev. Biol. Stand. 41: 225-234). As part of the early development of MVA as a pre-smallpox vaccine, there were clinical trials using MVA-517 in combination with Lister Elstree (Stickl (1974), Prev. Med. 3: 97-101; Stickl and Hochstein-Mintzel (1971), Munch. Med. Wochenschr. 113: 1149-1153) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), Zentralbl. Bacteriol. (B) 167: 375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies. MVA-575 was deposited on Dec. 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells (Blanchard et al. (1998), J. Gen. Virol. 79:1159-1167; Carroll & Moss (1997), Virology 238:198-211; U.S. Pat. No. 5,185,146; Ambrosini et al. (1999), J. Neurosci. Res. 55: 569). It is assumed that the results reported in these publications have been obtained with various known strains of MVA, since the viruses used essentially differ in their properties, particularly in their growth behavior in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic. MVA was further passaged by Bavarian Nordic and is designated MVA-BN, a representative sample of which was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

MVA-BN can attach to and enter human cells where virally-encoded genes are expressed very efficiently. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome (E. Harrer et al. (2005), Antivir. Ther. 10(2):285-300; A. Cosma et al. (2003), Vaccine 22(1):21-9; M. Di Nicola et al. (2003), Hum. Gene Ther. 14(14):1347-1360; M. Di Nicola et al. (2004), Clin. Cancer Res., 10(16):5381-5390).

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat (Boukamp et al (1988), J. Cell Biol. 106: 761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893, both of which are incorporated by reference herein in their entirety.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the present invention can be prepared using methods known in the art, such as those described in WO/2002/042480 and WO/2002/24224, the relevant disclosures of which are incorporated herein by references.

In another aspect, replication deficient MVA viral strains can also be suitable such as strain MVA-572, MVA-575 or any similarly attenuated MVA strain. Also suitable can be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

In a preferred embodiment of the present invention, the MVA vector(s) comprise a nucleic acid that encode one or more antigenic proteins selected from the group consisting of GPs of Zaire ebolavirus (EBOV), GPs of Sudan ebolavirus (SUDV), GPs of Marburg virus (MARV), the NP of Tai Forest virus and GPs or NPs substantially similar thereto.

The filovirus protein can be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding antigenic determinants of a filovirus envelope glycoprotein and/or a further filovirus protein. The heterologous nucleotide sequences can, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding antigenic determinants of a filovirus envelope glycoprotein and/or a further filovirus protein.

The number of insertion sites of MVA comprising heterologous nucleotide sequences encoding antigenic determinants of a filovirus protein can be 1, 2, 3, 4, 5, 6, 7, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in Molecular Virology: A Practical Approach (A. J. Davison & R. M. Elliott (Eds.), The Practical Approach Series, IRL Press at Oxford University Press, Oxford, UK (1993) (see, e.g., Chapter 9: Expression of genes by Vaccinia virus vectors) and Current Protocols in Molecular Biology (John Wiley & Son, Inc. (1998) (see, e.g., Chapter 16, Section IV: Expression of proteins in mammalian cells using vaccinia viral vector).

For the generation of the various recombinant MVAs disclosed herein, different methods can be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter.

Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome, such as MVA, cloned as a bacterial artificial chromosome (BAC) and a linear foreign sequence flanked with DNA sequences homologous to sequences flanking the desired site of integration in the vaccinia virus genome.

The heterologous filovirus gene can be under the control of (i.e., operably linked to) one or more poxvirus promoters. In certain embodiments, the poxvirus promoter is a Pr7.5 promoter, a hybrid early/late promoter, or a PrS promoter, a PrS5E promoter, a synthetic or natural early or late promoter, or a cowpox virus ATI promoter.

Immunogenic Compositions

Immunogenic compositions are compositions comprising an immunologically effective amount of purified or partially purified adenovirus or MVA vectors for use in the invention. The vector comprises a nucleic acid encoding an antigenic protein of a Marburg virus. The antigenic protein of a Marburg virus encoded by the adenovirus vector can be the same antigenic protein of a Marburg that is encoded by the MVA vector, or the Marburg virus antigenic proteins encoded by the adenovirus and the MVA vectors can be different but share at least one antigenic determinant.

In one embodiment of the invention, the adenovirus vector comprises a nucleic acid encoding a GP from a Marburg virus, such as the GP of MARV-Angola (e.g., that having the amino acid sequence of SEQ ID NO:3), or MARV-Musoke (e.g., that having the amino acid sequence of SEQ ID NO:4), and the MVA vector comprises a nucleic acid encoding the same GP from the Marburg virus.

In another embodiment of the invention, the adenovirus vector comprises a nucleic acid encoding a GP from one isolate of Marburg virus, such as the GP of MARV-Angola (e.g., that having the amino acid sequence of SEQ ID NO:3), and the MVA vector comprises a nucleic acid encoding a GP from a different isolate of Marburg virus, such as the GP of MARV-Musoke (e.g., that having the amino acid sequence of SEQ ID NO:4), or vice versa.

Said compositions can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In addition to adenovirus or MVA vectors comprising a nucleic acid encoding an antigenic protein of a Marburg virus, the compositions of the invention can comprise other filovirus antigen(s) or nucleic acid encoding other filovirus antigen(s), or the priming or boosting inoculations can comprise other filovirus antigens or nucleic acid encoding other filovirus antigen(s). The other antigens and nucleic acids expressing the other antigens can be, for example, from one or more additional filovirus subtypes, such as Ebola. The nucleic acid encoding the other filovirus antigen(s) can be included in the same adenovirus or MVA vectors that encode the antigenic protein of a Marburg virus. They can also be present on other vectors in the compositions or the priming or boosting inoculations.

The immunogenic compositions useful in the invention can comprise adjuvants.

Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

Method for Inducing Protective Immunity Against a Marburg Virus Infection

The present invention provides a method of priming and boosting an immune response to a Marburg virus in an individual using an adenoviral vector in combination with an MVA vector.

According to one general aspect of the present invention, a method of inducing an immune response against a Marburg virus in a subject comprises:

a. administering to the subject a first composition comprising an immunologically effective amount of an adenovirus vector comprising a nucleic acid encoding a first antigenic protein of a Marburg virus; and
b. administering to the subject a second composition comprising an immunologically effective amount of an MVA vector comprising a nucleic acid encoding a second antigenic protein of a Marburg virus, preferably the nucleic acid further encoding one or more antigenic proteins of one or more additional filovirus subtypes wherein steps (a) and (b) are conducted in either order, and the first and second antigenic proteins share at least one antigenic determinant. In a preferred embodiment the later step is conducted 1-12 weeks after the first step. In a more preferred embodiment the later step is conducted 4 or 8 weeks after the first step.

In one embodiment of the disclosed methods, an adenovirus vector is used to prime the immune response, and an MVA vector is used to boost the immune response about 1-12 weeks after the priming vaccination. Boosting compositions are generally administered weeks or months after administration of the priming composition, for example, about 1 or 2 weeks or 3 weeks, or 4 weeks, or 6 weeks, or 8 weeks, or 12 weeks, or 16 weeks, or 20 weeks, or 24 weeks, or 28 weeks, or 32 weeks or one to two years after administration of the priming composition.

In a preferred embodiment of the present invention, the adenovirus vectors disclosed herein include a rAd26 or rAd35 vector. In one exemplary embodiment, an rAd26 or rAd35 vector is used to prime the immune response, and an MVA vector is used to boost the immune response, or vice versa.

In a more preferred embodiment according to this method, an rAd26 vector is used for the priming followed by a boosting with an MVA vector. Preferably, the boosting composition is administered 1-12 weeks after priming, more preferably 1, 2, 4 or 8 weeks after priming. In a preferred embodiment, the boosting composition is administered 8 weeks after priming. In another preferred embodiment, the boosting composition is administered 1 week after priming. In another preferred embodiment, the boosting composition is administered 2 weeks after priming. In another preferred embodiment, the boosting composition is administered 4 weeks after priming.

In a more preferred embodiment according to this method, an MVA vector is used for the priming followed by a boosting with a rAd26 vector. Preferably, the boosting composition is administered 1-12 weeks after priming, more preferably 1, 2, 4 or 8 weeks after priming. In a preferred embodiment, the boosting composition is administered 8 weeks after priming. In another preferred embodiment, the boosting composition is administered 1 week after priming. In another preferred embodiment, the boosting composition is administered 2 weeks after priming. In another preferred embodiment, the boosting composition is administered 4 weeks after priming.

The present invention is also related to methods of inducing immune responses against a Marburg virus by priming and boosting the immune responses, preferably with a combination of heterologous vectors.

According to another aspect of the present invention, a method of inducing an immune response against a Marburg virus in a subject comprises:

a. administering to the subject an immunologically effective amount of a rAd26 or rAd35 vector comprising nucleic acids encoding a first glycoprotein of a Marburg virus; and
b. administering to the subject an immunologically effective amount of one or more MVA vectors comprising one or more nucleic acids encoding a second glycoprotein of a Marburg virus and one or more glycoproteins of additional subtypes of filoviruses, wherein steps (a) and (b) are conducted in either order, and the first and second glycoprotein share at least one antigenic determinant.

In one or more embodiments of the described method, one or more of rAd26 or rAd35 vectors are used to prime the immune response, and one or more of MVA vectors are used to boost the immune response, or vice versa.

In a preferred embodiment according to the method herein, one or more of rAd26 vectors are used for the priming followed by a boosting with one or more of MVA vectors. Preferably, the boosting inoculation is administered 1-12 weeks after priming, more preferably 1, 2, 4 or 8 weeks after priming.

The antigens of a Marburg virus in the respective priming and boosting compositions (however many boosting compositions are employed) need not be identical, but should share antigenic determinants or be substantially similar to each other.

Administration of the immunogenic compositions comprising the vectors is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the adenovirus vector. An alternative is the use of a needleless injection device to administer the composition (using, e.g., Biojector™) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed. Typically, administration will have a prophylactic aim to generate an immune response against a filovirus antigen before infection or development of symptoms. Diseases and disorders that can be treated or prevented in accordance with the present invention include those in which an immune response can play a protective or therapeutic role. In other embodiments, the adenovirus and MVA vectors can be administered for post-exposure prophylactics.

The immunogenic compositions containing the adenovirus vectors are administered to a subject, giving rise to an anti-Marburg virus immune response in the subject. An amount of a composition sufficient to induce a detectable immune response is defined to be an "immunologically effective dose." As shown below, the immunogenic compositions of the invention induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus and MVA vectors and optional formulation of such particles into compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the adenovirus or MVA vectors.

In one exemplary regimen, the adenovirus vector is administered (e.g., intramuscularly) in a volume ranging between about 100 μl to about 10 ml containing concentrations of about $10^4$ to $10^{12}$ virus particles/ml. Preferably, the adenovirus vector is administered in a volume ranging between 0.25 and 1.0 ml. More preferably the adenovirus vector is administered in a volume of 0.5 ml.

Typically, the adenovirus is administered in an amount of about $10^9$ to about $10^{12}$ viral particles (vp) to a human subject during one administration, more typically in an amount of about $10^{10}$ to about $10^{12}$ vp. In a preferred embodiment, the adenovirus vector is administered in an amount of about $1\times10^{11}$ vp. In a preferred embodiment, the adenovirus vector is administered in an amount of about $5\times10^{10}$ vp. In another preferred embodiment, the adenovirus vector is administered in an amount of about $0.8\times10^{10}$ vp. In another preferred embodiment, the adenovirus vector is administered in an amount of about $2\times10^{10}$ vp. In another preferred embodiment, the adenovirus vector is administered in an amount of about $4\times10^{10}$ vp. The human adenovirus vector can be administered in a concentration of about $10^7$ vp/ml, $10^8$ vp/ml, $10^9$ vp/ml, $10^{10}$ vp/ml, $5\times10^{10}$ vp/ml, $10^{11}$ vp/ml, or $10^{12}$ vp/ml.

In certain embodiments, adenoviruses are formulated as a trivalent composition, wherein three adenoviruses with each a different insert, are mixed together.

In another exemplary regimen, the MVA vector is administered (e.g. intramuscularly) in a volume ranging between about 100 μl to about 10 ml of saline solution containing a dose of about $1\times10^7$TCID$_{50}$ to $1\times10^9$ TCID$_{50}$ (50% Tissue Culture Infective Dose) or Inf.U. (Infectious Unit or InfU). Preferably, the MVA vector is administered in a volume ranging between 0.25 and 1.0 ml. More preferably the MVA vector is administered in a volume of 0.5 ml.

Typically, the MVA vector is administered in a dose of about $1\times10^7$ TCID$_{50}$ to $1\times10^9$ TCID$_{50}$ (or Inf.U.) to a human subject during one administration. In a preferred embodiment, the MVA vector is administered in an amount of about $5\times10^7$ TCID$_{50}$ to $5\times10^8$ TCID$_{50}$ (or Inf.U.). In a more preferred embodiment, the MVA vector is administered in an amount of about $5\times10^7$ TCID$_{50}$ (or Inf.U.). In a more preferred embodiment, the MVA vector is administered in an amount of about $1\times10^8$ TCID$_{50}$ (or Inf.U.). In another preferred embodiment, the MVA vector is administered in an amount of about $1.9\times10^8$ TCID$_{50}$ (or Inf.U). In yet another preferred embodiment, the MVA vector is administered in an amount of about $4.4\times10^8$ TCID$_{50}$ (or Inf.U.). In another preferred embodiment, the MVA vector is administered in an amount of about $1.3\times10^8$ TCID$_{50}$ (or Inf.U). In another preferred embodiment, the MVA vector is administered in an amount of about $1.0\times10^8$ TCID$_{50}$(or Inf.U). In another preferred embodiment, the MVA vector is administered in an amount of about $2.5\times10^8$ TCID$_{50}$ (or Inf.U). In a more preferred embodiment, the MVA vector is administered in an amount of about $5\times10^8$ TCID$_{50}$ (or Inf.U.)

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

The invention provides also the following non-limiting embodiments:

1. A vaccine combination comprising
   (i) a first composition comprising an immunologically effective amount of an adenovirus vector comprising a nucleic acid encoding a first antigenic protein of a Marburg virus, together with a pharmaceutically acceptable carrier; and
   (ii) a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, together with a pharmaceutically acceptable carrier;

wherein one of the compositions is a priming composition and the other composition is a boosting composition, and the first and second antigenic proteins share at least one antigenic determinant.

2. The vaccine combination according to embodiment 1, wherein the first and second antigenic proteins are from the same Marburg virus.
3. The vaccine combination according to embodiment 1, wherein the first and second antigenic proteins are from different Marburg viruses.

4. The vaccine combination according to any of embodiments 1-3, wherein the first antigenic protein comprises the amino acid sequence of SEQ ID NO:3 or SEQ ID NO:4.
5. The vaccine combination according to any of embodiments 1-4, wherein the second antigenic protein comprises the amino acid sequence of SEQ ID NO:3 or SEQ ID NO:4.
6. The vaccine combination according to any of embodiments 1 and 3-5, wherein the first antigenic protein comprises the amino acid sequence of SEQ ID NO:3, and the second antigenic protein comprises the amino acid sequence of SEQ ID NO: 4.
7. The vaccine combination according to any of embodiments 1-6, wherein the first composition comprises one or more adenovirus vectors comprising one or more nucleic acids encoding antigenic proteins having the amino acid sequences of SEQ ID NO: 1, SEQ ID NO: 2, and SEQ ID NO: 3.
8. The vaccine combination according to any one of embodiments 6 and 7, wherein the second composition comprises one or more MVA vectors comprising one or more nucleic acids encoding antigenic proteins having the amino acid sequences of SEQ ID NO: 1, SEQ ID NO: 2, SEQ ID NO: 4, and SEQ ID NO: 5.
9. The vaccine combination according to any one of embodiments 1-8, wherein the adenovirus vector is rAd26 or rAd35 vector, and the MVA vector is MVA-BN vector.
10. A vaccine combination comprising:
   (i) a first composition comprising an immunologically effective amount of an rAd26 vector comprising a nucleic acid encoding a first antigenic protein of a Marburg virus having the amino acid sequence of SEQ ID NO:3, together with a pharmaceutically acceptable carrier; and
   (ii) a second composition comprising an immunologically effective amount of an MVA vector comprising a nucleic acid encoding a second antigenic protein of a Marburg virus having the amino acid sequence of SEQ ID NO:3 or SEQ ID NO:4, together with a pharmaceutically acceptable carrier;
   wherein the first compositions is a priming composition and the second composition is a boosting composition.
11. The vaccine combination according to embodiment 10, wherein the MVA vector comprises a nucleic acid encoding the second antigenic protein having the amino acid sequence of SEQ ID NO:4.
12. The vaccine combination according to embodiment 10 or 11, wherein the MVA vector comprises a nucleic acid encoding antigenic proteins having the amino acid sequences of SEQ ID NO: 1, SEQ ID NO: 2, SEQ ID NO: 4 and SEQ ID NO: 5; optionally, the first composition further comprises one or more adenovirus vectors comprising one or more nucleic acids encoding antigenic proteins having the amino acid sequences of SEQ ID NO: 1 and SEQ ID NO: 2.
13. A vaccine combination according to any one of embodiments 1-12 for use in generating a protective immune response against at least one Marburg virus in a subject, wherein the first composition is used for priming said immune response and the second composition is used for boosting said immune response.
14. A vaccine combination according to any one of embodiments 1-12 for use in generating a protective immune response against at least one Marburg virus in a subject, wherein the second composition is used for priming said immune response and the first composition is used for boosting said immune response.
15. A method of inducing an immune response against a Marburg virus in a subject, the method comprising:
   a. administering to the subject a first composition comprising an immunologically effective amount of an adenovirus vector comprising a nucleic acid encoding a first antigenic protein of a Marburg virus; and
   b. administering to the subject a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype,
   wherein steps (a) and (b) are conducted in either order, and the first and second antigenic proteins share at least one antigenic determinant.
16. The method according to embodiment 15, wherein the first and second antigenic proteins are from the same Marburg virus.
17. The method according to embodiment 15, wherein the first and second antigenic proteins are from different Marburg viruses.
18. The method according to any of embodiments 15-17, wherein the first antigenic protein comprises the amino acid sequence of SEQ ID NO:3 or SEQ ID NO:4.
19. The method according to any of embodiments 15-18, wherein the second antigenic protein comprises the amino acid sequence of SEQ ID NO:3 or SEQ ID NO:4.
20. The method according to any of embodiments 15 and 17-19, wherein the first antigenic protein comprises the amino acid sequence of SEQ ID NO:3, and the second antigenic protein comprises the amino acid sequence of SEQ ID NO: 4.
21. The method according to any of embodiments 15-20, wherein the first composition comprises one or more adenovirus vectors comprising one or more nucleic acids encoding antigenic proteins having the amino acid sequences of SEQ ID NO: 1, SEQ ID NO: 2, and SEQ ID NO: 3.
22. The method according to any one of embodiments 20 and 21, wherein the second composition comprises one or more MVA vectors comprising one or more nucleic acids encoding antigenic proteins having the amino acid sequences of SEQ ID NO: 1, SEQ ID NO: 2, SEQ ID NO: 4, and SEQ ID NO: 5.
23. The method according to any one of embodiments 15-22, wherein the adenovirus vector is rAd26 or rAd35 vector, and the MVA vector is MVA-BN vector.
24. The method according to any one of embodiments 15-23, wherein step (b) is conducted 1-12 weeks, preferably 4-8 weeks, after step (a).
25. A method of inducing an immune response against a Marburg virus in a subject, the method comprising:
   a. administering to the subject a first composition comprising an immunologically effective amount of an rAd26 vector comprising a nucleic acid encoding a first antigenic protein of a Marburg virus having the amino acid sequence of SEQ ID NO:3; and
   b. administering to the subject a second composition comprising an immunologically effective amount of an MVA vector comprising a nucleic acid encoding a second antigenic protein of a Marburg virus having the amino acid sequence of SEQ ID NO:3 or SEQ ID NO:4.

wherein step (b) is conducted 1-12 weeks, preferably 4 or 8 weeks, after step (a).

26. The method according to embodiment 25, wherein the MVA vector comprises a nucleic acid encoding the second antigenic protein having the amino acid sequence of SEQ ID NO:4.

27. The method according to embodiment 25 or 26, wherein the MVA vector comprises a nucleic acid encoding antigenic proteins having the amino acid sequences of SEQ ID NO: 1, SEQ ID NO: 2, SEQ ID NO: 4 and SEQ ID NO: 5; optionally, the first composition further comprises one or more adenovirus vectors comprising one or more nucleic acids encoding antigenic proteins having the amino acid sequences of SEQ ID NO: 1 and SEQ ID NO: 2.

28. A kit comprising:

a. a first composition comprising an immunologically effective amount of an adenovirus vector comprising a nucleic acid encoding a first antigenic protein of a Marburg virus, together with a pharmaceutically acceptable carrier; and b. a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, together with a pharmaceutically acceptable carrier;

wherein one of the compositions is a priming composition and the other composition is a boosting composition, and the first and second antigenic proteins share at least one antigenic determinant.

29. The kit according to embodiment 28, wherein the first and second antigenic proteins are from the same Marburg virus.

30. The kit according to embodiment 28, wherein the first and second antigenic proteins are from different Marburg viruses.

31. The kit according to any of embodiments 28-30, wherein the first antigenic protein comprises the amino acid sequence of SEQ ID NO:3 or SEQ ID NO:4.

32. The kit according to any of embodiments 28-31, wherein the second antigenic protein comprises the amino acid sequence of SEQ ID NO:3 or SEQ ID NO:4.

33. The kit according to any of embodiments 28 and 30-32, wherein the first antigenic protein comprises the amino acid sequence of SEQ ID NO:3, and the second antigenic protein comprises the amino acid sequence of SEQ ID NO: 4.

34. The kit according to any of embodiments 28-33, wherein the first composition comprises one or more adenovirus vectors comprising one or more nucleic acids encoding antigenic proteins having the amino acid sequences of SEQ ID NO: 1, SEQ ID NO: 2, and SEQ ID NO: 3.

35. The kit according to any one of embodiments 33 and 34, wherein the second composition comprises one or more MVA vectors comprising one or more nucleic acids encoding antigenic proteins having the amino acid sequences of SEQ ID NO: 1, SEQ ID NO: 2, SEQ ID NO: 4, and SEQ ID NO: 5.

36. The kit according to any one of embodiments 28-35, wherein the adenovirus vector is rAd26 or rAd35 vector, and the MVA vector is MVA-BN vector 37. A kit comprising:

(i) a first composition comprising an immunologically effective amount of an rAd26 vector comprising a nucleic acid encoding a first antigenic protein of a Marburg virus having the amino acid sequence of SEQ ID NO:3, together with a pharmaceutically acceptable carrier; and (ii) a second composition comprising an immunologically effective amount of an MVA vector comprising a nucleic acid encoding a second antigenic protein of a Marburg virus having the amino acid sequence of SEQ ID NO:3 or SEQ ID NO:4, together with a pharmaceutically acceptable carrier;

wherein the first compositions is a priming composition and the second composition is a boosting composition.

38. The kit according to embodiment 37, wherein the MVA vector comprises a nucleic acid encoding the second antigenic protein having the amino acid sequence of SEQ ID NO:4.

39. The kit according to embodiment 37 or 38, wherein the MVA vector comprises a nucleic acid encoding antigenic proteins having the amino acid sequences of SEQ ID NO: 1, SEQ ID NO: 2, SEQ ID NO: 4 and SEQ ID NO: 5; optionally, the first composition further comprises one or more adenovirus vectors comprising one or more nucleic acids encoding antigenic proteins having the amino acid sequences of SEQ ID NO: 1 and SEQ ID NO: 2.

40. The kit according to any one of embodiments 28-39 for use in generating a protective immune response against at least one Marburg virus in a subject, wherein the first composition is used for priming said immune response and the second composition is used for boosting said immune response.

41. The kit according to any one of embodiments 28-39 for use in generating a protective immune response against at least one Marburg virus in a subject, wherein the second composition is used for priming said immune response and the first composition is used for boosting said immune response.

42. A use of a vaccine combination according to any one of embodiments 1-14 for manufacturing a pharmaceutical composition or medicament for inducing an immune response against a Marburg virus in a subject, wherein the first composition is used for priming said immune response and the second composition is used for boosting said immune response.

43. A use of a vaccine combination according to any one of embodiments 1-14 for manufacturing a pharmaceutical composition or medicament for inducing an immune response against a Marburg virus in a subject, wherein the second composition is used for priming said immune response and the first composition is used for boosting said immune response.

44. A use of a kit according to any one of embodiments 28-39 for manufacturing a pharmaceutical composition or medicament for inducing an immune response against a Marburg virus in a subject, wherein the first composition is used for priming said immune response and the second composition is used for boosting said immune response.

45. A use of a kit according to any one of embodiments 28-39 for manufacturing a pharmaceutical composition or medicament for inducing an immune response against a Marburg virus in a subject, wherein the second composition is used for priming said immune response and the first composition is used for boosting said immune response.

The compositions of the invention can be administered alone or in combination with other treatments, either simultaneously or sequentially dependent upon the condition to be treated.

EXAMPLES

The following examples are offered to illustrate, but not to limit the claimed invention.

Example 1

A study was performed to assess the immunogenicity and protective efficacy of heterologous prime-boost regimens consisting of trivalent Ad26 and MVA-BN-Filo with an 8 week interval between prime and boost, in Cynomolgus macaques (*Macaca fascicularis*) (NHPs). The first regimen consisted of a trivalent Ad26 prime vaccine (Ad26.Filo, containing Ad26.MARVA, Ad26.ZEBOV and Ad26.SEBOV) and MVA-BN-Filo as a boost vaccine, administered 8 weeks later. The second regimen consisted of an MVA-BN-Filo prime vaccine, followed by trivalent Ad26.Filo as a boost vaccine, administered 8 weeks later. All immunizations were performed intramuscularly.

Vaccine Materials

The trivalent Ad26 (Ad26.Filo) contains recombinant Ad26 vectors expressing EBOV Mayinga glycoprotein (GP) (SEQ ID NO:1), SUDV Gulu GP (SEQ ID NO:2) and MARV Angola GP (SEQ ID NO:3), wherein each rAd26 vector expressed one single antigenic protein (GP). The MVA-multi vector (MVA-BN-Filo) expresses 4 different antigenic proteins: EBOV Mayinga GP (SEQ ID NO:1); SUDV Gulu GP (SEQ ID NO:2); MARV Musoke GP (SEQ ID NO:4); and Ebola virus Tali forest/Ivory Coast (TAFV) Nucleoprotein (NP) (SEQ ID NO:5).

In this study 12 NHPs were included that were divided over 3 experimental groups (Table 1). Group 1 served as a negative control. Group 2 and 3 assessed the immunogenicity and protective efficacy of trivalent Ad26.Filo/MVA-BN-Filo immunization with either Ad26.Filo or MVA-BN-Filo as prime vaccine. Ad26.Filo was administered at a dose of $1.2\times10^{11}$ vp ($4\times10^{10}$ vp per vector) and MVA-BN-Filo at a dose of $5\times10^{8}$ InfU.

TABLE 1

Experimental Grouping of Protection Study in Non-human Primates Challenged With MARV

| Group | Immunization 1 (Dose 1) | Immunization 2 (Dose 2) | Immunization Schedule (Weeks) | Challenge | Group Size N |
|---|---|---|---|---|---|
| 1 | negative control (empty vector) | negative control (TBS) | 0-8 | MARV (Angola) | 2 |
| 2 | Ad26.Filo ($1.2\times10^{11}$ vp) | MVA-BN-Filo ($5\times10^{8}$ InfU) | 0-8 | MARV (Angola) | 5 |
| 3 | MVA-BN-Filo ($5\times10^{8}$ InfU) | Ad26.Filo ($1.2\times10^{11}$ vp) | 0-8 | MARV (Angola) | 5 |

Abbreviations:
TBS: Tris-buffered saline;
Inf.U.: Infectious Unit;
vp: viral particles.

Immunogenicity

Blood samples were taken prior to prime vaccination, and 8, 10 and 11 weeks post prime, and analyzed for MARV GP-binding antibodies (see FIG. 1) by MARV GP-specific Enzyme Linked Immnunosorbent Assay (ELISA). As expected, no antibody response was observed in NHP immunized with saline (FIG. 1, left). The prime-immunization with the Ad26.Filo vectors induced a MARV GP specific antibody response in all animals immunized with the trivalent vaccine, and MVA-BN-Filo induced a strong boost in all NHPs. MVA-BN-Filo priming elicited lower titers than Ad26.Filo priming, but after boosting with Ad26.Filo, the post-boost responses were similar in both groups 2 and 3.

Protective Efficacy

Figure 2:
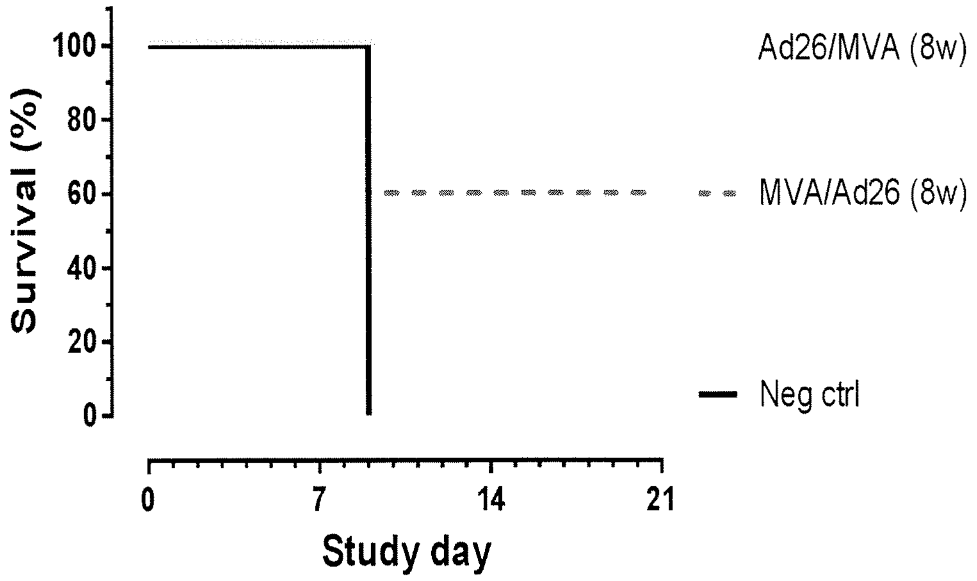
FIG. 2 shows the protective efficacy of different vaccine combinations and negative controls (Neg ctrl) in vaccinated NHPs after challenge with Marburg Angola virus.

All animals were challenged 4 weeks after the last immunization with 1000 pfu of MARV Angola wild-type P3 challenge virus via the intramuscular route in a Biosafety Level 4 containment unit. Negative controls succumbed to the infection by day 9 post-challenge (FIG. 2). All (5/5) animals immunized with heterologous Ad26.Filo/MVA-BN-Filo prime/boost immunization survived until the end of the experiment (FIG. 2). Three out of five (3/5) animals immunized with MVA-BN-Filo/Ad26 survived the challenge (FIG. 2).

Example 2

The immunogenicity of the monovalent Ad26.MARVA/MVA-BN-Filo heterologous prime boost was confirmed in an experiment, in which 5 NHPs were immunized with Ad26.MARV at $4\times10^{10}$ vp on day 0 and boosted with MVA-BN-Filo at a dose of $5\times10^{8}$ InfU on day 56. In parallel, 10 NHPs were immunized with trivalent Ad26.Filo (at a dose of $1.2\times10^{11}$ vp, containing $4\times10^{10}$ vp Ad26.MARV) and boosted with MVA-BN-Filo at a dose of $5\times10^{8}$ InfU on day 56.

Figure 3:
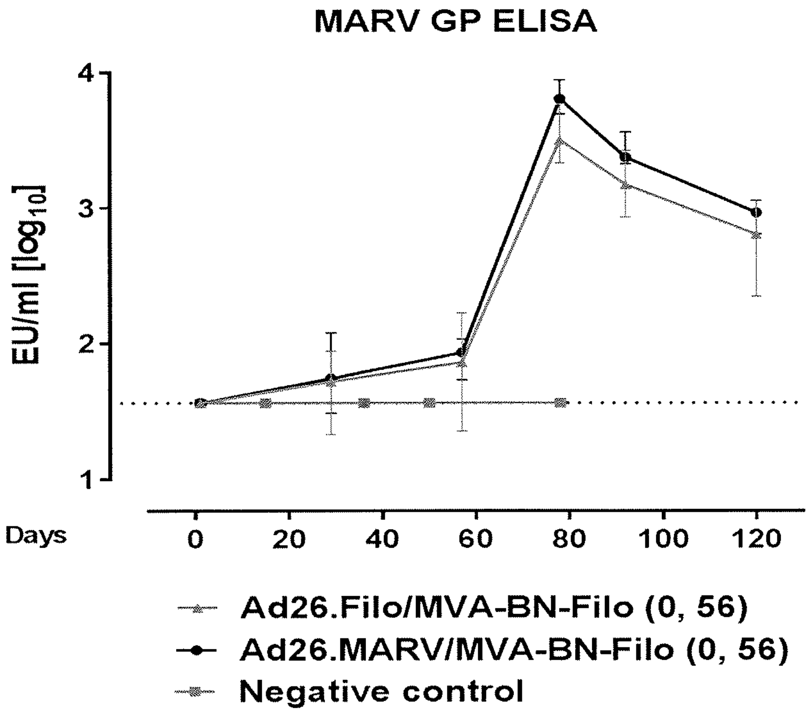
FIG. 3 is a plot of the kinetic of MARV GP-binding antibodies in serum samples taken from NHPs vaccinated with different vaccine combinations as analyzed by a MARV GP-specific ELISA, the mean log 10-transformed ELISA concentrations (ELISA Units per ml, EU/ml) with standard deviations are shown.

In this study, MARV GP specific immune response was determined at 4 and 8 weeks post prime, and at 3 and 5 weeks post boost using a MARV GP-specific ELISA. This ELISA was performed using purified recombinant MARV Angola GP directly coated on the ELISA plate. Monovalent Ad26.MARV/MVA-BN-Filo immunization elicited higher or comparable anti-MARV GP antibody titers (FIG. 3) as compared with the trivalent Ad26.Filo/MVA-BN-Filo immunization. Therefore, it is likely that the protective efficacy observed after Ad26.Filo/MVA-BN-Filo immunization (see, e.g., Example 1) would also be observed after Ad26.MARVA/MVA-BN-Filo immunization.

Example 3

A study will be performed to assess the immunogenicity and protective efficacy of a prime-boost regimen at 0-8 week intervals in Cynomolgus macaques (*Macaca fascicularis*) (NHPs), using a monovalent Ad26.MARVA vaccine as a prime and a MVA-BN-Filo as a boost. All immunizations are performed intramuscularly.

Vaccine Materials

The Ad26.MARVA vector expresses the MARV Angola GP (SEQ ID NO:3).

The MVA-multi vector (MVA-BN-Filo) expresses 4 different antigenic proteins: EBOV Mayinga GP (SEQ ID NO:1); SUDV Gulu GP (SEQ ID NO:2); MARV Musoke GP (SEQ ID NO:4); and Tai forest virus (TAFV) NP (SEQ ID NO:5).

The Ad26.MARVA ($5\times10^{10}$ vp) is used as a prime for the 0-8 week regimen, and will be combined with a boost of $1\times10^8$ InfU of MVA-BN-Filo (6 NHPs). Two NHPs will be immunized with saline and TBS as negative immunization control for the study. The grouping of this study is summarized in Table 2.

All animals will be challenged 6 weeks after the last immunization with 1000 pfu of MARV Angola wild-type P3 challenge virus via the aerosol route in a Biosafety Level 4 laboratory.

TABLE 2

Experimental Grouping of Protection Study in Non-human Primates Challenged With aerosolized MARV

| Group | Immunization 1 (Dose 1) | Immunization 2 (Dose 2) | Immunization Schedule (Weeks) | Challenge After 6 Weeks | Group Size N |
|---|---|---|---|---|---|
| 1 | negative control (TBS) | negative control (saline) | 6-8 | MARV (Angola) | 2 |
| 2 | Ad26. MARVA ($5\times10^{10}$ vp) | MVA-BN-Filo ($5\times10^8$ InfU) | 0-8 | MARV (Angola) | 6 |

Abbreviations:
TBS: Tris-buffered saline;
InfU: Infectious Unit;
vp: viral particles.

Endpoints in this study will be survival/nonsurvival. Nonsurvival is defined by an animal having terminal illness or being moribund. Animals' health will be evaluated on a daily clinical observation score sheet.

Immunogenicity

Blood will be sampled prior to each immunization and 1, 3 and 5 weeks after the last immunization for analyses of the immune response. The immune response in NHP will be characterized with respect to Filovirus GP-binding and neutralizing antibodies (ELISA) as well as cytokine producing T cells (ELISpot and Intracellular Cytokine Staining).

EDTA or heparin whole blood will be collected and processed for PBMC and plasma. PBMC will be used in an IFN-g ELISPOT and an Intracellular Cytokine Staining assay using Marburg Angola GP peptides (15-mers overlapping by 11, spanning the entire MARV Angola GP) together with a DMSO only negative control and a stimulation positive control. Additionally, whole blood without anticoagulant will be processed for serum to be assayed in a MARVA GP specific ELISA and Virus Neutralization Assay.

Example 4

A clinical study will be performed in humans for evaluating the safety, tolerability and immunogenicity of regimens using Ad26.MARVA at a dose of $5\times10^{10}$ vp or $1\times10^{11}$ vp as prime followed by a boost 56 days later with MVA-BN-Filo at a dose of $5\times10^8$ $TCID_{50}$ or $1\times10^8$ $TCID_{50}$, respectively.

The study will be a randomized, placebo-controlled, observer-blind study being conducted in 36 healthy adult subjects. The study will consist of a vaccination period in which subjects will be vaccinated at baseline (Day 1) followed by a boost on Day 57, and a post-boost follow-up until all subjects have had their 35-day post-boost visit (Day 92) or discontinued earlier.

Subjects will be enrolled into 2 different groups of 18 healthy subjects each. Overall, subjects will be randomized within a group in a 5:1 ratio to receive active vaccine or placebo (0.9% saline) through IM injections (0.5 ml) as follows:

Ad26.MARVA ($1\times10^{11}$ vp) on Day 1, followed by a booster of MVA-BN-Filo ($1\times10^8$ InfU) on Day 57 (Group 2), or Ad26.MARVA ($5\times10^{10}$ vp) on Day 1, followed by a booster of MVA-BN-Filo ($5\times10^8$ InfU) on Day 57 (Group 2).

The exemplary study vaccination schedules are summarized in Table 3.

TABLE 3

Study Vaccination Schedules

| Group | N | | Day 1 | Day 57 |
|---|---|---|---|---|
| 1 | 18 | 15 | Ad26.MARVA $1\times10^{11}$ vp | MVA-BN-Filo $1\times10^8$ InfU |
| | | 3 | placebo (0.9% saline) | placebo (0.9% saline) |
| 2 | 18 | 15 | Ad26.MARVA $5\times10^{10}$ vp | MVA-BN-Filo $5\times10^8$ InfU |
| | | 3 | placebo (0.9% saline) | placebo (0.9% saline) |

N: number of subjects to receive study vaccine;
InfU: Infectious Unit;
vp: viral particles Vaccine Materials:

The Ad26.MARVA vector expresses the MARV Angola GP (SEQ ID NO:3).

The MVA-multi vector (MVA-BN-Filo) expresses 4 different antigenic proteins: EBOV Mayinga GP (SEQ ID NO:1); SUDV Gulu GP (SEQ ID NO:2); MARV Musoke GP (SEQ ID NO:4); and TO forest virus (TAFV) NP (SEQ ID NO:5).

Safety will be assessed by collection of solicited local and systemic adverse events, unsolicited adverse events and serious adverse events, and by physical examination. In addition, standard chemistry, hematologic (including coagulation parameters) and urinalysis parameters will be assessed at multiple time points.

Immunogenicity will be assessed using the immunologic assays summarized in Tables 4 and 5. The exploratory assay package may include, but is not limited to, the listed assays.

TABLE 4

Summary of Immunologic Assays (Serology)

| Assay | Purpose |
|---|---|
| Secondary endpoints | |
| ELISA | Analysis of antibodies binding to MARV GP |
| Exploratory endpoints | |
| Virus neutralization assay | Analysis of neutralizing antibodies to MARV GP |
| Adenovirus/MVA neutralization assay | Neutralizing antibodies to adenovirus/MVA |

MARV: Marburg virus;
ELISA: enzyme-linked immunosorbent assay;
GP: glycoprotein;
MVA: Modified Vaccinia Ankara

TABLE 5

Summary of Immunologic Assays (Cellular)

| Assay | Purpose |
|---|---|
| Exploratory endpoints | |
| ELISpot | T-cell IFN-γ responses to MARV GP |
| ICS of frozen PBMC | Analysis of T-cell responses to MARV GP (including CD4/8, IL-2, IFN-γ, TNF-α and/or activation markers) |

MARV: Marburg virus;
ELISpot: enzyme-linked immunospot;
GP: glycoprotein;
ICS: intracellular cytokine staining;
IFN: interferon;
IL: interleukin;
PBMC: peripheral blood mononuclear cells;
TNF: tumor necrosis factor It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A combination of an immunogenic composition comprising a. a first composition consisting of an immunologically effective amount of an adenovirus vector comprising a nucleic acid encoding a first antigenic protein of a Marburg virus, together with a pharmaceutically acceptable carrier, wherein the first antigenic protein has the amino acid sequence of SEQ ID NO: 3, and wherein the first antigenic protein is the only antigen protein encoded by the adenovirus vector; and b. a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, together with a pharmaceutically acceptable carrier;

wherein the first antigenic protein and the second antigenic protein share at least one antigenic determinant, and the first composition is the priming composition and the second composition is the boosting composition.

2. The combination according to claim 1, wherein the second antigenic protein has the amino acid sequence of SEQ ID NO: 3 or SEQ ID NO: 4.

3. The combination according to claim 1, wherein the MVA vector in the second composition comprises a nucleic acid encoding antigenic proteins having the amino acid sequences of SEQ ID NO: 1, SEQ ID NO: 2, SEQ ID NO: 4, and SEQ ID NO: 5.

4. The combination according to claim 1, wherein the adenovirus vector is an rAd26 or rAd35 vector.

5. The combination according to claim 1, wherein the adenovirus vector is an rAd26 vector, and the MVA vector is a MVA-BN vector.

6. The combination according to claim 1 for generating a protective immune response against at least one Marburg virus in a subject.

7. A method of inducing an immune response against a Marburg virus in a subject, the method comprising:

a. administering to the subject a first composition consisting of an immunologically effective amount of an adenovirus vector comprising a nucleic acid encoding a first antigenic protein of a Marburg virus, wherein the first antigenic protein has the amino acid sequence of SEQ ID NO: 3, and wherein the first antigenic protein is the only antigenic protein encoded by the adenovirus vector; and b. administering to the subject a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, wherein the first antigenic protein and the second antigenic protein share at least one antigenic determinant, and step (b) is conducted 1-12 weeks, preferably 4 or 8 weeks, after step (a).

8. The method according to claim 7, wherein the second antigenic protein has the amino acid sequence of SEQ ID NO: 3 or SEQ ID NO: 4.

9. The method according to claim 7, wherein the MVA vector in the second composition comprises a nucleic acid encoding antigenic proteins having the amino acid sequences of SEQ ID NO: 1, SEQ ID NO: 2, SEQ ID NO: 4, and SEQ ID NO: 5.

10. The method according to claim 7, wherein the adenovirus vector is an rAd26 or rAd35 vector.

11. The method according to claim 7, wherein the adenovirus vector is an rAd26 vector, and the MVA vector is a MVA-BN vector.

12. A kit comprising:

a. a first composition consisting of an immunologically effective amount of an adenovirus vector comprising a nucleic acid encoding a first antigenic protein of a Marburg virus, together with a pharmaceutically acceptable carrier, wherein the first antigenic protein has the amino acid sequence of SEQ ID NO: 3, and wherein the first antigenic protein is the only antigenic protein encoded by the adenovirus vector; and b. a second composition comprising an immunologically effective amount of an MVA vector comprising a nucleic acid encoding a second antigenic protein of a Marburg virus, preferably the nucleic acid further encoding one or more antigenic proteins of at least one additional filovirus subtype, together with a pharmaceutically acceptable carrier;

wherein the first antigenic protein and the second antigenic protein share at least one antigenic determinant, and the first composition is the priming composition and the second composition is the boosting composition.

13. The kit according to claim 12, wherein the second antigenic protein has the amino acid sequence of SEQ ID NO: 3 or SEQ ID NO: 4.

14. The kit according to claim 12, wherein the MVA vector in the second composition comprises a nucleic acid encoding antigenic proteins having the amino acid sequences of SEQ ID NO: 1, SEQ ID NO: 2, SEQ ID NO: 4, and SEQ ID NO: 5.

15. The kit according to claim 12, wherein the adenovirus vector is an rAd26 or rAd35 vector.

16. The kit according to claim 12, wherein the adenovirus vector is an rAd26 vector, and the MVA vector is a MVA-BN vector.

17. The kit according to claim 12, for generating an immune response against at least one Marburg virus in a subject.

18. A combination according to claim 1 for manufacturing a pharmaceutical composition or medicament to induce an immune response against a Marburg virus in a subject.

* * * * *